(12) United States Patent
Orban

(10) Patent No.: US 8,735,359 B2
(45) Date of Patent: May 27, 2014

(54) COMBINATIONS OF MODALITIES FOR THE TREATMENT OF DIABETES

(75) Inventor: Tihamer Orban, Brookline, MA (US)

(73) Assignee: Orban Biotech LLC, Brookline, MA (US)

( * ) Notice: Subject to any disclaimer, the term of this patent is extended or adjusted under 35 U.S.C. 154(b) by 0 days.

(21) Appl. No.: 13/534,571

(22) Filed: Jun. 27, 2012

(65) Prior Publication Data

US 2013/0315904 A1 Nov. 28, 2013

(51) Int. Cl.
| | | |
|---|---|---|
| *A61K 38/28* | (2006.01) | |
| *A61K 39/395* | (2006.01) | |
| *A61K 38/16* | (2006.01) | |
| *A61K 38/17* | (2006.01) | |
| *A61K 39/00* | (2006.01) | |
| *C07K 14/62* | (2006.01) | |
| *C07K 14/47* | (2006.01) | |
| *C07K 14/705* | (2006.01) | |

(52) U.S. Cl.
CPC ............ *A61K 38/28* (2013.01); *A61K 38/1774* (2013.01); *A61K 39/0008* (2013.01); *A61K 2039/55566* (2013.01); *C07K 14/62* (2013.01); *C07K 14/4713* (2013.01); *C07K 14/70521* (2013.01); *C07K 2319/00* (2013.01); *C07K 2319/30* (2013.01)
USPC ...................................... 514/21.2; 424/134.1

(58) Field of Classification Search
CPC .... C07K 14/62; C07K 14/4713; C07K 14/47; C07K 2319/00; C07K 2319/30; A61K 39/0008
See application file for complete search history.

(56) References Cited

U.S. PATENT DOCUMENTS

| | | | |
|---|---|---|---|
| 5,434,131 | A | 7/1995 | Linsley et al. |
| 5,814,321 | A | 9/1998 | Miyahara et al. |
| 5,844,095 | A | 12/1998 | Linsley et al. |
| 5,851,795 | A | 12/1998 | Linsley et al. |
| 5,976,538 | A | 11/1999 | Hilgers et al. |
| 6,110,746 | A | 8/2000 | Cohen et al. |
| 6,235,282 | B1 | 5/2001 | Riviere et al. |
| 6,299,884 | B1 | 10/2001 | Van Nest et al. |
| 7,041,634 | B2 | 5/2006 | Weber et al. |
| 7,304,033 | B2 | 12/2007 | Larsen et al. |
| 7,455,835 | B2 | 11/2008 | Cohen et al. |
| 2002/0114814 | A1 * | 8/2002 | Gray et al. .................. 424/178.1 |
| 2004/0136998 | A1 | 7/2004 | Bander |
| 2004/0151725 | A1 * | 8/2004 | Gray et al. .................. 424/178.1 |
| 2006/0183670 | A1 | 8/2006 | Orban |
| 2009/0016968 | A1 | 1/2009 | Wang et al. |
| 2009/0142308 | A1 | 6/2009 | Orban et al. |
| 2011/0250225 | A1 | 10/2011 | Fotin-Mleczek et al. |
| 2011/0311529 | A1 | 12/2011 | Cohen et al. |
| 2012/0258094 | A1 * | 10/2012 | Cohen et al. ............... 424/133.1 |
| 2013/0316375 | A1 | 11/2013 | Orban |

FOREIGN PATENT DOCUMENTS

| | | |
|---|---|---|
| RU | 2 283 847 C2 | 9/2006 |
| WO | 2009/120341 A2 | 10/2009 |
| WO | 2012/001647 A2 | 1/2012 |
| WO | 2012/015903 A1 | 2/2012 |

OTHER PUBLICATIONS

Chatenoud et al., Cold Spring Harb. Perspect. Med., Jun. 7, 2012; 2:a007716, 18 pages.*
Phillips et al., Clin. Devel. Immunol., 2011:432016. doi: 10.1155/2011/432016. Epub Jul. 18, 2011, 18 pages.*
Sanderson et al., J. Clin. Oncol. (2005); 23: 741-750.*
Pozzilli et al., Immunotherapy, Jul. 2012, 4: 655-658.*
[No Author Listed] American Diabetes Assoc. Diabetes Care 2011;33(Suppl 1):S11-61.
[No Author Listed] Diabetes Control and Complications Trial Research Group. N Engl J Med 1993;329:977-86.
Abrams et al. J Clin Invest 1999;103:1243-52.
Agresti, Categorical Data Analysis. New York, New York. John Wiley and Sons. 1990;Chapter 3:36-78.
Allison et al. Mol Immunol 1991;28:279-84.
Beebe et al. Am J Epidemiol 1972;95(4):337-46.
Bingley et al. Diabetes 1994;43:1304-10.
Bluestone et al. Immunity 2006;24:233-8.
Davenport, Ann Allerg 1968;26:288-92.
Genant et al., Ann Rheum Dis 2008; 67:1084-9.
Hunter et al. Vaccine 1991;9:250-6.
Lan et al. Biometrika 1983;70:659-63.
Lenschow et al., J Exp Med 1995;181:1145-55.
Liping et al. Diabetes Aug. 2001;50(8):1735-40.
Lo et al. Am J Transplant 2011;11:22-3.
Marelli-Berg et al. A Trends Immunol 2007;28:267-73.
Mease et al. Arthritis Rheum 2011;63:939-48.
Muir et al. J Clin Invest 1995;95:628-34.
Orban et al. Diabetes 1999;48(Suppl 1):A216.
Orban et al. J Autoimmun Jun. 2010;34(4):408-15.
Orban et al. Lancet 2011;378(9789):412-9.
Ramiya et al. J Autoimmun 1996;9:349-56.
Ruperto et al. Lancet 2008;372:383-91.
Salk et al. Science 1977;195;834-47.
Schneider et al. Clin Immunol Mar. 2012;142(3):402-3.
Trauger et al. J Acquir Immune Defic Syndr Hum Retrovirol 1995;10(Supp 2):S74-82.
Trauger et al. J Infect Dis 1994;169:1256-64.
Turner et al. AIDS 1994;8:1429-35.
Verge et al. Diabetes 1996;45:926-33.

(Continued)

*Primary Examiner* — Ilia Ouspenski
(74) *Attorney, Agent, or Firm* — Nutter McClennen & Fish LLP; John J Penny, Jr.; Isaac A. Hubner

(57) ABSTRACT

A method of treating, preventing, or delaying the progression of Type 1 diabetes mellitus by administering an effective amount of a fusion protein composition comprising a T-cell co-stimulation antagonist and a portion of an immunoglobulin molecule and an effective amount of a Type 1 diabetes autoantigen. The method includes, for example, administering a cytotoxic T-lymphocyte-associated antigen 4 (CTLA4) molecule and a Type 1 diabetes autoantigen. Pharmaceutical compositions are also provided herewith.

5 Claims, 4 Drawing Sheets

(56) References Cited

OTHER PUBLICATIONS

Verge et al. Diabetes 1998;47:1857-66.
Vincenti et al. N Engl J Med 2005;353:770-81.
Aanstoot et al. J Clin Invest Jun. 15, 1996;97(12):2772-83.
Alcalde et al. J Autoimmun 1996;9(4):525-8.
Boitard et al. PNAS 1992;89(1):172-6.
Castano et al. J Clin Endocrinol Metab 1991;73(6):1197-201.
Christgau et al. J Biol Chem 1991;266(31):21257-64.
Dionisi et al. Ann Ist Super Sanita 1997;33(3):433-5.
Dotta et al. Diabetes Sep. 1996;45(9):1193-6.
Elias et al. Eur J Immunol 1995;25(10):2851-7.
Kasimiotis et al. Diabetes 2000;49(4):555-61.
Keller et al. Lancet 1993;341:927-8.
Lan et al. DNA Cell Biol 1994;13:505-14.
Muir et al. Diabetes Metab Rev 1993;9:279-87.
Pietropaolo et al. J Clin Invest 1993;92:359-71.
Rabin et al. J Immunol 1994;152(6):3183-8.
Tagami et al. J Biol Chem Nov. 13, 2002;277(5):3085-92.
Xie et al. J Immunol 1997;159:3662-7.
Zhang et al. Diabetes 1997;46:40-3.
[No Author Listed] Mayo Foundation for Medical Education and Research, 2012, accessed at mayoclinic.com/health/type-1-diabetes/DS00329 on Sep. 13, 2012, 20 pages.
[No Author Listed] NCT00505375, ClinicalTrials.gov, updated Jan. 31, 2011, 4 pages.
Aly et al., Am. J. Therapeutics (2005) 12: 481-490.
Blazar et al., Infusion of anti-B7.1 (CD80) and anti-B7.2 (CD86) monoclonal antibodies inhibits murine graft-versus-host disease lethality in part via direct effects on CD4+ and CD8+ T cells. J Immunol. Oct. 15, 1996;157(8):3250-9.
Chittasupho et al., Ther. Deliv. 2011, 2: 873-889.
Driessens et al., Immunol. Rev. 2009, 229: 126-144.
Fukai et al., Graefe's Arch. Clin. Exp. Ophthalmol., 1999, 237:928-933.
Sanderson et al., J. Clin. Oncol. (2005); 23:741-750.
Sturmhoefel et al., Cancer research, 1999, 59:4964-4972.
Swiniarski et al., Clinical Immunology, 1999, 92:235-245.
Huurman et al., Differential inhibition of autoreactive memory- and alloreactive naive T cell responses by soluble cytotoxic T lymphocyte antigen 4 (sCTLA4), CTLA4Ig and; LEA29Y. Clin Exp Immunol. Dec. 2007;150(3):487-93. Epub Oct. 9, 2007.
International Search Report and Written Opinion for Application No. PCT/US2013/042627, issued Sep. 12, 2013. (7 pages).
International Search Report and Written Opinion for Application No. PCT/US2013/048237, issued Oct. 18, 2013. (6 pages).
Kretowski et al., Naïve, memory and CD45RA+CD45RO+ T helper cell subpopulations in preclinical phase of diabetes type 1 (prediabetes). Przeglag Lekarski, 2001;58(1):16-9. Polish. Abstract only.
Palmer et al., C-peptide is the appropriate outcome measure for type 1 diabetes clinical trials to preserve beta-cell function: report of an ADA workshop, Oct. 21-22, 2001. Diabetes. Jan. 2004;53(1):250-64.
Roep, The role of T-cells in the pathogenesis of Type 1 diabetes: from cause to cure. Diabetologia. Mar. 2003;46 (3):305-21. Epub Mar. 22, 2003.
Yu et al., DPT-1 Participating Investigators. Expression of GAD65 and islet cell antibody (ICA512) autoantibodies among cytoplasmic ICA+ relatives is associated with eligibility for the Diabetes Prevention Trial-Type 1. Diabetes. Aug. 2001;50(8):1735-40.
Glinka et al., Protective regulatory T cell generation in autoimmune diabetes by DNA covaccination with islet antigens and a selective CTLA-4 ligand. Mol Ther. Oct. 2006;14(4):578-87. Epub Jun. 21, 2006.
International Search Report and Written Opinion for Application No. PCT/US2013/048247, issued Oct. 18, 2013. (6 pages).

\* cited by examiner

COMBINATIONS OF MODALITIES FOR THE TREATMENT OF DIABETES

FIELD OF THE INVENTION

The present invention relates generally to the field of autoimmune disease and specifically to the treatment, prevention, or delayed progression of Type 1 diabetes mellitus using a combination of a CTLA4 fusion protein and a Type 1 diabetes autoantigen.

BACKGROUND

The most common form of Type 1 diabetes mellitus (T1DM) is an immune-mediated disease where insulin-secreting β-cells are destroyed by an autoimmune response. There are a number of genetic and environmental factors associated with the onset of the disease, which involves the progressive inflammatory infiltration of pancreatic islets containing immunocytes targeted specifically to insulin-secreting β-cells. This pathology develops over an indeterminate period of time (months to years). While the discovery of insulin allowed for the treatment of T1DM, there is currently no cure. The most common form of Type 1 diabetes mellitus is immune-mediated, in which insulin-producing β cells are destroyed. Yet, at the time of diagnosis, most patients still have appreciable amounts of insulin production. Preservation of residual β-cell function is highly desirable because it can reduce short-term and long-term complications of the disease.

Several clinical trials have been undertaken in an attempt to arrest autoimmunity in Type 1 diabetes with immunomodulatory agents or antigen-based treatments. Most notably, trials of anti-CD3, anti-CD20, and a GAD-65 antigen vaccine have shown some efficacy in preservation of β-cell function as evidenced by stimulated C-peptide secretion. T cells play a central part in autoimmunity associated with Type 1 diabetes.

Reintroduction of autoantigen, such as insulin B-chain, in incomplete Freund's adjuvant (IFA), has also been contemplated for the treatment or delayed progression of Type 1 diabetes. This has been studied in animal models of diabetes (NOD mice) (Muir et al. (1995) J Clin Invest 95:628-634; Orban et al. (1999) Diabetes 48 Supp.1:A216-A217; Ramiya et al. (1996) J Autoimmun 9:349-356); U.S. Pat Pub. 2006/0183670 and U.S. Pat. Pub. 2009/0142308 and in humans. Orban et al., J. Autoimmun. (2010 June);34(4):408-15.

However, there is need for additional new therapies for Type 1 diabetes mellitus that are able to halt or slow autoimmune β-cell destruction and thus prevent development of Type 1 diabetes, or at least prolong onset of the disease for as long a period of time as possible.

SUMMARY

In accordance with certain embodiments of the present invention relate to methods of treating diabetes mellitus in a subject comprising: administering an effective amount of a fusion protein composition comprising a T-cell co-stimulation antagonist such as extracellular domain of CTLA4, an effective fragment of the extracellular domain or immunologically active variant of the extracellular domain and a portion of an immunoglobulin molecule and an effective amount of a Type 1 diabetes autoantigen such as preproinsulin, GAD 65, ICA512/IA-2, HSP60, carboxypeptidase H, peripherin, and ganglioside or an immunologically active fragment or variant thereof to the subject. In some embodiments, the preproinsulin fragment is insulin B-chain or an immunologically active fragment or variant thereof such as amino acids 33-47 of SEQ ID NO:1 (i.e., B-chain 29-23)

In some embodiments, the subject has Type 1 diabetes mellitus with residual beta-cell function. In some embodiments, the T-cell co-stimulation antagonist binds a B7 (CD80/86) antigen expressed on B cells and/or on antigen presenting cells (APCs). In yet other embodiments, the B7 antigen is expressed on B cells and on APCs.

In some embodiments, the method is effective for preventing the onset of diabetes. In other embodiments, the method is effective for delaying the onset of diabetes by at least, for example, 3 months, 6, months, 9 months, 1 year, 1.5 years, 2 years, 3 years, or more. In some embodiments, the method further comprises determining levels of C-peptide in blood samples taken from the subject over time as an indicator of effectiveness of the treatment.

In yet other embodiments of the present invention, there is provided a pharmaceutical composition comprising: (a) a cytotoxic T-lymphocyte-associated antigen 4 (CTLA4) fusion protein, (b) an autoantigen selected from the group consisting of: preproinsulin, GAD 65, ICA512/IA-2, HSP60, carboxypeptidase H, peripherin, and ganglioside or an immunologically active fragment or variant thereof, and (c) a pharmaceutically acceptable carrier.

In some embodiments, the pharmaceutical composition is provided in an oil-based carrier such as IFA or Montanide ISA. In some embodiments, the pharmaceutical composition comprises about 250 mg to about 2000 mg of the fusion protein and about 0.5 to about 10 mg of the Type 1 diabetes autoantigen.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the applicant's teachings in any way.

Figure 1:
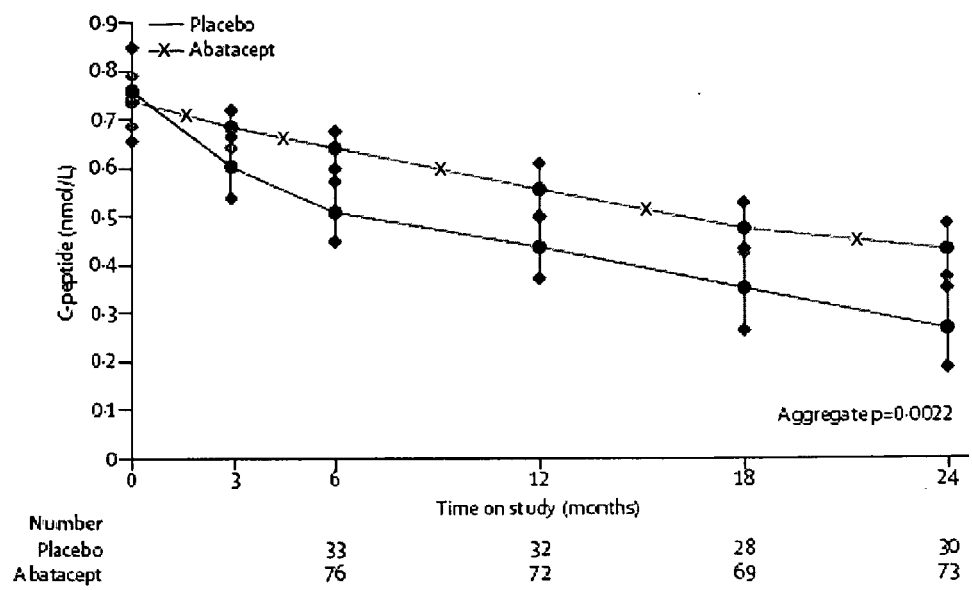
FIG. 1 is the population mean of stimulated C-peptide 2-h AUC mean over time for each treatment group. The estimates are from the ANCOVA model adjusting for age, sex, baseline value of C-peptide, and treatment assignment. Y-axis is on a log(y+1) scale. Error bars show 95% CIs. AUC=area under the curve.

It will be understood that the drawings are exemplary only and that all reference to the drawings is made for the purpose of illustration only, and is not intended to limit the scope of the embodiments described herein below in any way.

DETAILED DESCRIPTION

It has been found that a combination of a CTLA4 molecule and insulin-B chain in IFA can be used for the treatment, prevention, or delayed progression of Type 1 diabetes mellitus in a subject.

Preservation of residual β-cell function (as measured by peak C-peptide ≥0·2 nmol/L) is highly desirable because it can reduce short-term and long-term complications of the disease. Several clinical trials have been undertaken in an attempt to arrest autoimmunity in Type 1 diabetes with immunomodulatory agents or antigen-based treatments. Most notably, trials of anti-CD3, anti-CD20, and a GAD-65 antigen vaccine have shown some efficacy in preservation of β-cell function as evidenced by stimulated C-peptide secretion. C-peptide is a protein that is produced in the body along with insulin. In a healthy pancreas, preproinsulin is secreted with an A-chain, C-peptide, a B-chain, and a signal sequence. The signal sequence is cut off, leaving proinsulin. Then the C-peptide is cut out, leaving the A-chain and B-chain to form insulin. Since C-peptide and insulin are present in equimolar amounts, it is a highly reliable marker for insulin production and the health of pancreatic β cells.

T cells play a central part in autoimmunity associated with Type 1 diabetes. To become fully activated and autoaggressive, T cells are believed to need at least two crucial signals. (Marelli-Berg F M, Okkenhaug K, Mirenda V. A *Trends Immunol* 2007; 28: 267-73.) The first signal is an interaction between an antigen in the groove of the MHC molecule on antigen-presenting cells and the T-cell receptor (TCR). The most important second signal is the interaction between CD80 and CD86 on the antigen presenting cells (APCs) and CD28 on the T cells. This costimulatory second signal is needed for full activation of cells, and without it T cells do not become functional. Therefore, co-stimulation blockade has been proposed as a therapeutic modality for autoimmunity and transplantation. (Bluestone J A, St Clair E W, Turka L A. *Immunity* 2006; 24: 233-38.)

Cytotoxic T-lymphocyte-associated antigen 4 (CTLA4), which is also known as CD152, is a protein involved in the regulation of the immune system. Naturally occurring CTLA4 is described in U.S. Pat. Nos. 5,434,131, 5,844,095, and 5,851,795. Natural CTLA4 proteins are encoded by the CTLA4 gene. CTLA4 is a cell surface protein, having an N-terminal extracellular domain, a transmembrane domain, and a C-terminal cytoplasmic domain. The extracellular domain binds to and/or interferes with target antigens, such as CD80 and CD86, serves as nature natural break of T cell stimulation. In some embodiments, the extracellular domain of the CTLA4 molecule begins with methionine at position +1 and ends at aspartic acid at position +124; in other embodiments, the extracellular domain begins with alanine at position −1 and ends at aspartic acid at position +124.

A CTLA4 molecule is a molecule comprising a cytotoxic T-lymphocyte-associated antigen 4 (CTLA4) extracellular domain. In some embodiments, the extracellular domain of CTLA4 comprises a portion of the CTLA4 protein that recognizes and binds to at least one B7 (CD80/86) antigen such as a B7 antigen expressed on B cells and on antigen presenting cells (APCs). The B-cells and APCs may be activated. The extracellular domain may also include fragments or derivatives of CTLA4 that bind a B7 antigen. The CTLA4 extracellular domain can also recognize and bind CD80 and/or CD86. The extracellular domain may also include fragments or derivatives of CTLA4 that bind a binds CD80 and/or CD86.

The CTLA4 molecule may be a fusion protein, where a fusion protein is defined as one or more amino acid sequences joined together using methods well known in the art. The joined amino acid sequences thereby form one fusion protein. In some embodiments, the CTLA4 molecule contains at least a portion of an immunoglobulin, such as the Fc portion of an immunoglobulin. In some embodiments, the CTLA4 molecule is an isolated and purified CTLA4 molecule.

In some embodiments, the CTLA4 molecule is a protein containing at least a portion of an immunoglobulin, such as the Fc portion of an immunoglobulin. In some embodiments, the CTLA4 molecule is an isolated and purified CTLA4 molecule.

In some preferred embodiments, the CTLA4 molecule is abatacept. Abatacept is a soluble fusion protein that consists of the extracellular domain of human CTLA-4 linked to the modified Fc (hinge, CH2, and CH3 domains) portion of human immunoglobulin G1 (IgG1). Abatacept is produced by recombinant DNA technology in a mammalian cell expression system. The apparent molecular weight of abatacept is 92 kilodaltons.

Abatacept was developed for use in adult rheumatoid arthritis and juvenile idiopathic arthritis and is indicated for reducing signs and symptoms, inducing major clinical response, inhibiting the progression of structural damage, and improving physical function in adult patients with moderately to severely active rheumatoid arthritis.

Abatacept was developed by Bristol-Myers Squibb and is disclosed, for example, in U.S. Pat. No. 5,851,795, U.S. Pat. No. 7,455,835, and U.S. Pat. Pub. 20011/311529. Abatacept, under the trade name ORENCIA, may be used as monotherapy or concomitantly with disease-modifying antirheumatic drugs (DMARDs) other than tumor necrosis factor (TNF) antagonists. Abatacept is also indicated for reducing signs and symptoms in pediatric patients 6 years of age and older with moderately to severely active polyarticular juvenile idiopathic arthritis. Abatacept may be used as monotherapy or concomitantly with methotrexate (MTX). Since abatacept is a selective costimulation modulator and inhibits the costimulation of T cells, it should not be administered concomitantly with TNF antagonists.

Abatacept selectively binds to CD80 and CD86, thereby blocking the interaction with CD28 and interfering with T-cell activation. It inhibits naive T-cell activation, thus having the potential to selectively inhibit T-cell response to specific antigens instead of broad immunosuppression. Effector-memory T-cell responses are less dependent on CD28 co-stimulation and, presumably, are less inhibited by co-stimulation blockade. (Lo D J, Weaver T A, Stempora L, et al. *Am J Transplant* 2011; 11: 22-33.)

Studies in both animals and human beings have shown that interruption of the co-stimulatory second signal beneficially affects autoimmunity. Co-stimulation blockade with abatacept has been shown to have clinical effectiveness in psoriasis (Abrams J R, Lebwohl M G, Guzzo C A, et al. *J Clin Invest* 1999; 103: 1243-52) and psoriatic arthritis (Mease P, Genovese M C, Gladstein G, et al. *Arthritis Rheum* 2011; 63: 939-48) and is approved for treatment of rheumatoid arthritis, Genant H K, Peterfy C G, Westhovens R, et al. *Ann Rheum Dis* 2008; 67: 1084-89) including juvenile rheumatoid arthritis. (Ruperto N, Lovell D J, Quartier P, et al *Lancet* 2008; 372: 383-91.) Additionally, co-stimulation blockade has been effective in control of allograft rejection. (Vincenti F, Larsen C, Durrbach A. *N Engl J Med* 2005; 353: 770-81.) Moreover, Lenschow and coworkers (Lenschow D J, Ho S C, Sattar H, et al. *J Exp Med* 1995; 181: 1145-55) showed that costimulatory blockade with both an anti B7-2 monoclonal antibody and a CTLA4-immunoglobulin fusion protein prevented diabetes in the NOD mice model when administered prior to 10 weeks of age.

It has now been shown that co-stimulation modulation with T-cell co-stimulatory antagonists such as CTLA-4 compositions and in particular abatacept, halts or slows autoimmune β-cell destruction leading to preservation of C-peptide secretion in recently diagnosed patients with Type 1 diabetes by blocking the generation of autoaggressive T cells (Orban et al., *Lancet* 2011; 378 (9789): 412-9.)

There are many autoantigens considered to be important in human Type 1 diabetes mellitus. Several data suggest that insulin is a major antigen playing roles in the pathogenesis of the disease (Muir et al. (1993) Diabetes Metab. Rev 9:279-287). Insulin, a β-cell specific major protein is moderately immunogenic when used alone, and has been shown in a pilot human trial to have the effect of delaying the development of diabetes mellitus (Keller et al. (1993) Lancet 341:927-928). However, it must be injected daily over long periods of time to induce the desired effect. When insulin is used in humans, there is always a major concern about hypoglycemia and its sequels.

Immunogenic fragments or variants of insulin or preproinsulin lacking hypoglycemic effect are a safe choice for human use. For example, insulin B-chain (or immunogenic fragments and variants thereof without metabolic effect) can be used as an immune modulator to prevent or delay further loss of functional, residual β-cell mass, after the clinical onset of Type 1 diabetes in humans, without hypoglycemic effect. The reintroduction of autoantigen, e.g., insulin B-chain, in human subjects can act to change to autoimmune process triggering a protective immune response. The Th1/Th2 balance can change in favor of a protective Th2 type cell response and generation of regulatory immune cells, Tregs.

Autoantibodies against insulin, glutamic acid decarboxylase (GAD) and other islet cell autoantigens, e.g., ICA 512/IA-2 protein tyrosine phosphatase, ICA12, ICA69, are frequently found in newly diagnosed diabetic patients. Thus, Type 1 diabetes autoantigens useful in the methods of the invention include, e.g., preproinsulin or an immunologically active fragment thereof (e.g., preproinsulin fragment, insulin B-chain, A chain, C peptide or an immunologically active fragment thereof), and other islet cell autoantigens (ICA), e.g., GAD65, islet tyrosine phosphatase ICA512/IA-2, ICA12, ICA69 or immunologically active fragments thereof. Other Type 1 diabetes autoantigens include HSP60, carboxypeptidase H, peripherin, gangliosides (e.g., GM1-2, GM3) or immunologically active fragments thereof. Any of the Type 1 diabetes autoantigens described herein, or immunologically active fragments, analogs or derivatives thereof, are useful in the methods and compositions of the invention.

The insulin mRNA is translated as a 110 amino acid single chain precursor called preproinsulin, and removal of its signal peptide during insertion into the endoplasmic reticulum generates proinsulin. Proinsulin consists of three domains: an amino-terminal B-chain, a carboxy-terminal A chain and a connecting peptide in the middle known as the C peptide. Within the endoplasmic reticulum, proinsulin is exposed to several specific endopeptidases which excise the C peptide, thereby generating the mature form of insulin which consists of the A and B-chain. Insulin and free C peptide are packaged in the Golgi into secretory granules which accumulate in the cytoplasm. The preproinsulin peptide sequence is found in SEQ ID NO: 1.

Insulin A chain includes amino acids 90-110 of SEQ ID NO: 1. B-chain includes amino acids 25-54 of SEQ ID NO: 1. The connecting sequence (amino acids 55-89 of SEQ ID NO: 1) includes a pair of basic amino acids at either end. Proteolytic cleavage of proinsulin at these dibasic sequences liberates the insulin molecule and free C peptide, which includes amino acids 57-87 of SEQ ID NO:1. The human preproinsulin or an immunologically active fragment thereof, e.g., B-chain or an immunogenic fragment thereof, e.g., amino acids 33-47 of SEQ ID NO:1 (corresponding to residues 9-23 of the B-chain) or signal peptide sequence or other sequences of the preproinsulin, are useful as autoantigens in the methods and compositions described herein.

Gad65 is a primary β-cell antigen involved in the autoimmune response leading to insulin dependent diabetes mellitus (Christgau et al. (1991) J Biol. Chem. 266(31):21257-64). The presence of autoantibodies to GAD65 is used as a method of diagnosis of Type 1 diabetes. Gad65 is the 585 amino acid protein of SEQ ID NO:2. Changes in autoantibody titers and in GAD65AB isotypes reflecting the effect of administration can be used to characterize the regression in autoimmune process in diabetic or prediabetic patients. In addition, there will be changes in stimulated cytokine profile (in favor of Th2-cells) correlating with the effect of the autoantigen administration, which later may be used as humoral marker for regression of autoimmunity in Type 1 diabetes mellitus.

IA-2/ICA512, a member of the protein tyrosine phosphatase family, is another major autoantigen in Type 1 diabetes (Lan et al. DNA Cell Biol 13:505-514, 1994). 70% of diabetic patients have autoantibodies to IA-2, which appear years before the development of clinical disease. The IA-2 molecule (SEQ ID NO:3, below) is 979 amino acids in length and consists of an intracellular, transmembrane, and extracellular domain (Rabin et al. (1994) J. Immunol. 152 (6), 3183-3188). Autoantibodies are typically directed to the intracellular domain, e.g., amino acids 600-979 of SEQ ID NO:3 and fragments thereof (Zhang et al. (1997) Diabetes 46:40-43; Xie et al. (1997) J Immunol 159:3662-3667). The amino acid sequence of IA-2 is shown in SEQ ID NO: 3.

ICA 12 (Kasimiotis et al. (2000) Diabetes 49(4):555-61; Gen bank Accession No. AAD16237; SEQ ID NO:4) is one of a number of islet cell autoantigens associated with diabetes. The sequence of ICA12 is provided as SEQ ID NO: 4.

ICA69 is another autoantigen associated with Type 1 diabetes (Pietropaolo et al. J Clin Invest 1993; 92:359-371). The amino acid sequence of ICA69 is provided as SEQ ID NO: 5.

Glima 38 is a 38 kDa islet cell membrane autoantigen which is specifically immunoprecipitated with sera from a subset of prediabetic individuals and newly diagnosed Type 1 diabetic patients. Glima 38 is an amphiphilic membrane glycoprotein, specifically expressed in islet and neuronal cell lines, and thus shares the neuroendocrine expression patterns of GAD65 and IA2 (Aanstoot et al. J Clin Invest. Jun. 15, 1996; 97(12):2772-2783).

HSP60, e.g., an immunologically active fragment of HSP60, e.g., p277 (see Elias et al., Eur J Immunol 1995 25(10):2851-7), can also be used as an autoantigen in the methods and compositions described herein. Other useful epitopes of HSP 60 are described, e.g., in U.S. Pat. No. 6,110,746.

Carboxypeptidase H has been identified as an autoantigen, e.g., in pre-Type 1 diabetes patients (Castano et al. (1991) J Clin Endocrinol Metab. 73(6):1197-201; Alcalde et al. J.

Autoimmun. August 1996; 9(4):525-8.). Therefore, carboxypeptidase H or immunologically reactive fragments thereof (e.g., the 136-amino acid fragment of carboxypeptidase-H described in Castano, supra) can be used in the methods and compositions described herein.

Peripherin is a 58 KDa diabetes autoantigen identified in nod mice (Boitard et al. (1992) Proc Natl. Acad. Sci. USA 89(1):172-6. The human peripherin sequence is shown as SEQ ID NO:6.

Gangliosides can also be useful autoantigens in the methods and compositions described herein. Gangliosides are sialic acid-containing glycolipids which are formed by a hydrophobic portion, the ceramide, and a hydrophilic part, i.e. the oligosaccharide chain. Gangliosides are expressed, inter alia, in cytosol membranes of secretory granules of pancreatic islets. Auto-antibodies to gangliosides have been described in Type 1 diabetes, e.g., GM 1-2 ganglioside is an islet autoantigen in diabetes autoimmunity and is expressed by human native β cells (Dotta et al. Diabetes. September 1996; 45(9):1193-6). Gangliosides GT3, GD3 and GM-1 are also the target of autoantibodies associated with autoimmune diabetes (reviewed in Dionisi et al. Ann Ist Super Sanita 1997; 33(3):433-5). Ganglioside GM3 participates in the pathological conditions of insulin resistance (Tagami et al. J Biol Chem Nov. 13, 2001; online publication ahead of print).

Insulin B-chain is a preferred diabetes autoantigen. Human insulin B-chain for human vaccine use can be made by a standard solid-phase peptide synthesis. A procedure for effective solubilization of the insulin β-chain is described herein. In some embodiments, the autoantigen is human insulin B-chain (amino acids 25-54 of SEQ ID NO:1) or an immunologically active fragment, or variant thereof. In some embodiments, the B-chain or fragment thereof is not recombinant. For example, the B-chain or immunogenic fragment or variant thereof is a synthetic peptide, e.g., the B-chain is made by solid-phase synthesis. In some preferred embodiments, the B-chain is solubilized in urea. In some embodiments, the human insulin B-chain is denatured, e.g., solubilized in urea and DTT. In a preferred embodiment, the human insulin B-chain is between 30-70%, preferably between 40-60%, more preferably between 45-55% proportion weight by weight (w/w).

Thus, there is provided herein a method of treating, preventing, or delaying the progression of diabetes mellitus by administering CTLA4 and a Type 1 diabetes autoantigen. The two components may be administered simultaneously, sequentially, or with a separate time course (e.g., one in the morning and the other in the evening or in other different time courses related to each other).

The onset of T1DM may be delayed by the methods as described herein such that insulin is not needed by the subject for a longer length of time. Alternatively or in addition, the present method may extend the "honeymoon phase" in an already diabetic subject The honeymoon phase is where insulin is secreted by the pancreas, causing high blood sugar levels to subside, and resulting in normal or near normal glucose levels due to responses to insulin injections and treatment.

T1DM may be prevented in a subject by first selecting a subject who is susceptible to developing diabetes and administering a CTLA4 molecule and a Type 1 diabetes autoantigen as described herein. The subject who is susceptible to developing diabetes may be selected by the expression of one or more of: GAD65 autoantibodies (GAAs), ICA512 autoantibodies (ICA512AAs), or anti-insulin autoantibodies (IAAs). Each of these autoantibodies is associated with a risk of progression to autoimmune Type 1 diabetes. Expression of two or more of: GAD65 autoantibodies (GAAs), ICA512 autoantibodies (ICA512AAs), or anti-insulin autoantibodies (IAAs) is associated with a high risk of progression to autoimmune Type 1 diabetes. (Liping Yu et al., *Diabetes August* 2001 vol. 50 no. 8 1735-1740; Verge C F et al., *Diabetes* 45:926-933, 199; Verge C F. et al, *Diabetes* 47:1857-1866, 1998; and Bingley P J, et al., *Diabetes* 43:1304-1310, 1994).

T1DM may also be treated by the methods as described herein. The treatment is for subjects with residual beta-cell function or those no longer having any beta-cell function. The treatment may also be suggested for subjects provided exogenous beta-cells through transplant or injection or other beta cell replacement modalities (like embryonic or other stem cell therapies or other replacement modalities).

The combination of a CTLA4 molecule and the T1DM autoantigen as described herein may be administered as part of one or more pharmaceutical compositions. The methods of the invention can prevent diabetes mellitus, or prevent or delay loss of residual β-cell mass, providing a longer remission period reducing short term complications and/or delaying the onset of diabetes-related complications at a later stage of the life.

The CTLA4 molecule and T1DM autoantigen may be combined into a single pharmaceutical composition. Alternatively, the CTLA4 molecule is provided in one pharmaceutical composition and the T1DM autoantigen is provided in a separate pharmaceutical compositions. In this alternative, the two pharmaceutical compositions may have the same or different modes of administration and time course of administration.

The pharmaceutical composition as provided herewith may include a pharmaceutically acceptable carrier. The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical-Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds described herein including pharmaceutically acceptable carriers can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compositions as described herein may be administered with an adjuvant. The term "adjuvant" can be a compound that lacks significant activity administered alone but can potentiate the activity of another therapeutic agent. In some embodiments, an adjuvant is selected from the group consisting of buffers, anti-microbial preserving agents, surfactants, antioxidants, tonic regulators, antiseptics, thickeners and viscosity improvers. In some embodiments, the adjuvant is IFA or other oil based adjuvant is present between 30-70%, preferably between 40-60%, more preferably between 45-55% proportion weight by weight (w/w). In some embodiments, human insulin B-chain and IFA or other oil based adjuvant are present in about a 50/50 weight by weight ratio. In some embodiments, the pharmaceutical composition is free of contaminants, e.g., pyrogens.

In some embodiments, the autoantigen is lyophilized. In another aspect, the invention provides a pharmaceutical composition containing T1DM autoantigen that is made by the method of: combining T1DM autoantigen and an oil-based carrier, e.g., an oil-based adjuvant, e.g., IFA, or other oil based adjuvant, e.g., Montanide ISA (e.g., Montanide ISA51), and emulsifying the insulin B-chain and oil-based adjuvant. In some embodiments, the T1DM autoantigen is human insulin B-chain or preproinsulin or an immunologically active fragment or variant thereof which is combined with an oil-based carrier where the insulin B-chain and oil-based adjuvant are emulsified. In a preferred embodiment, human insulin β-chain and oil-based adjuvant are combined in a weight by weight ratio (w/w) of between 30/70 to 70/30, preferably between 40/60 to 60/40, preferably between 45/55 to 55/45, more preferably about a 50/50 w/w ratio. In a preferred embodiment, emulsification is performed with a high pressure syringe. In preferred embodiments, the oil-based carrier or adjuvant, and preferably the composition, does not include a bacterial component, e.g., a mycobacterial component.

In some embodiments, the T1DM autoantigen is a B-chain or preproinsulin or immunogenically active fragment or variant thereof and is solubilized in about 3 M to 8 M urea, preferably in about 3.5 M to 7 M urea, or about 4 M to 6 M urea. In a preferred embodiment, the B-chain or immunogenically active fragment or variant thereof is solubilized in about 3 M to 5 M urea, preferably in about 3.5 M to 4.5 M urea, most preferably in about 4 M urea. In a preferred embodiment, the β-chain or immunogenically active fragment or variant thereof is solubilized in 5-8 M urea, preferably in about 6 M to 7 M urea. Preferably, the B-chain is solubilized in the presence of a reducing agent, e.g., DTT or an equivalent reducing agent, e.g., 1 to 5 mg of DTT is added during the solubilization step.

In some embodiments, the composition comprising a Type 1 diabetes autoantigen and/or CTLA4 molecule also includes an oil-based carrier.

The oil-based carrier is a composition that includes at least 10% by weight of a natural or synthetic oil suitable for administration to a human in conjunction with a therapeutic agent is one preferred embodiment. In preferred embodiments, the carrier includes at least 20, 30, 50, 70, 80, 90, 95, 98, or 99% oil by weight. In some embodiments, the oil-based carrier can include less than 70, 60, 50, 40, 30 or 20% oil by weight. In preferred embodiments, the oil will be in the range of 10 to 95%, preferably 20 to 90% or 30 to 70% oil by weight. The oil should be chosen such that it provides for sustained release of a substance dispersed within it when administered to a subject. Suitable oils include mineral oil (e.g., Drakeol 6 VR light mineral oil), vegetable oil, squalene, or liquid paraffin. In some embodiments, the oil-based carrier can contain more than one type of oil. In some embodiments, the oil-based carrier can include an immune stimulator, e.g., an immunostimulating glucan, but it is much preferred that the oil-based carrier does not include an immune stimulator, e.g., an immunostimulating glucan, a bacterial component, e.g., a mycobacterial component. In a preferred embodiment, the oil-based carrier does not include an alum component.

While not wanting to be bound by theory, an oil based carrier is believed to work by triggering the immunocompetent cells, which are related to the inflammatory and protective immune response ability. An oil-based carrier can also act as an antigen vehicle and a slow release or long-term antigen presentation device. When injected into a subject, an oil-based carrier and antigen composition can form a depot of antigen at the injection site, thereby protecting the antigen from degradation. From this depot the antigen can be released slowly into the system and provides a prolonged antigen presentation as well as expanded total contact surface area and the attraction of inflammatory cells. Macrophages can digest most of the incorporated materials and present the processed antigens on their surface. From this depot the antigen can be released slowly into the system and provides a prolonged antigen supply to act as costimulatory modulator.

Oil based carriers optionally include an emulsifier or surfactant component. The emulsifier or surfactant (and the amount of emulsifier or surfactant) is chosen such that it facilitates the mixture or dispersion of a substance, e.g., an antigen preparation, with the oil. An oil-based carrier can include 0.1 to 50%, preferably 1 to 30%, more preferably 5 to 20% by weight of a surfactant or emulsifier. Examples of emulsifiers or surfactants include Arlacel A, mannide oleate (e.g., Montanide 80-mannide monooleate), anhydrous mannitol/oleic acid ester, polyoxyethylene or polyoxypropylene.

Incomplete Freund's adjuvant (IFA) is a preferred delivery vehicle for the autoantigen in humans. The methods of the invention can prevent diabetes mellitus, or prevent or delay loss of residual β-cell mass, providing a longer remission period and delaying the onset of diabetes related, usually progressive, complications at a later stage of the life.

An oil-based carrier or adjuvant typically consists of two components: (1) an oil, and (2) an emulsifier or surfactant, mixed with water. Suitable oils and emulsifiers are known in the art. For example, the oil can be mineral oil, vegetable oil, squalene or liquid paraffin. The emulsifier or surfactant can be, e.g., Arlacel A, mannide oleate, anhydrous mannitol/oleic acid ester, polyoxyethylene or polyoxypropylene. Exemplary oil-based adjuvants include conventional IFA, Montanide ISA adjuvants, or Hunter's TiterMax adjuvant. In preferred embodiments, the adjuvant includes 20 to 95%, preferably 30 to 90%, more preferably 40 to 70% by weight of an oil phase, and 0.1 to 50%, preferably 1 to 30%, more preferably 5 to 20% by weight of a surfactant or emulsifier. Various types of oil-based adjuvants are described, e.g., in U.S. Pat. No. 5,814,321, U.S. Pat. No. 6,299,884, U.S. Pat. No. 6,235,282, and U.S. Pat. No. 5,976,538.

IFA is typically a mixture of a non-metabolizable oil (e.g., mineral oil), water, and a surfactant (e.g., Arlacel A). Unlike Complete Freund's Adjuvant (CFA), IFA does not contain a bacterial component, e.g., mycobacteria. The first large-scale vaccinations using IFA in humans took place on US military personnel (Davenport (1968) Ann Allergy 26:288-292;

Beebe et al., (1972) Am J Epidemiol 95:337-346; Salk & Salk (1977) Science 195:834-847). The findings were essentially negative with respect to malignancy, allergic diseases and collagenosis, but there was evidence that some men had a cyst like reaction at the site of inoculation. Later studies confirmed that these side effects were due to incorrect administration i.e. they were given erroneously s.c. instead of i.m. From these experiments, IFA was regarded by some as unsuitable for human purposes, although it has remained widely used in animal research. In recent years, newer forms of IFA have been shown safe for human use in HIV immunotherapy or therapeutic vaccinations (Turner et al. (1994) AIDS 8:1429-1435; Trauger et al. (1995) J Acquir Immune Defic Syndr Hum Retrovirol 10 Supp2:S74-82; Trauger et al. (1994) J Infect Dis 169:1256-1264).

Montanide ISA Adjuvants (Seppic, Paris, France) are a group of oil/surfactant based adjuvants in which different surfactants are combined with either a non-metabolizable mineral oil, a metabolizable oil, or a mixture of the two. They are prepared for use as an emulsion with aqueous Ag solution. The surfactant for Montanide ISA 50 (ISA=Incomplete Seppic Adjuvant) is mannide oleate, a major component of the surfactant in Freund's adjuvants. The surfactants of the Montanide group undergo strict quality control to guard against contamination by any substances that could cause excessive inflammation, as has been found for some lots of Arlacel A used in Freund's adjuvant. The various Montanide ISA group of adjuvants are used as water-in-oil emulsions, oil-in-water emulsions, or water-in-oil-in-water emulsions. The different adjuvants accommodate different aqueous phase/oil phase ratios, because of the variety of surfactant and oil combinations.

Hunter's TiterMax (CytRx Corp., Norcross, Ga.) is an oil/surfactant-based adjuvant prepared as a water-in-oil emulsion in a manner similar to that used for conventional Freund's adjuvants. However, it uses a metabolizable oil (squalene) and a nonionic surfactant that has good protein antigen-binding capacity as well as adjuvant activity. The adjuvant activity may relate, in part, to the surfactant's ability to activate complement and bind complement components, as this helps target the Ag to follicular dendritic cells in the spleen and lymph nodes. The surfactant used in the commercially available adjuvant is one of a number of synthetic nonionic block copolymers of polyoxyethylene and polyoxypropylene developed by Hunter (Hunter et al., 1991 Vaccine 9:250-256). The utilization of copolymer-coated microparticles to stabilize the emulsion permits formation of stable emulsions with less than 20% oil, an important factor in minimizing total adjuvant injected.

An adjuvant can be used with antigens to elicit cell-mediated immunity and the production of antibodies of protective isotypes (IgG2a in mice and IgG1 in primates). Different types of adjuvants share similar side effects, such as a reaction at the injection site and pyrogenicity. Alum, a commonly used adjuvant for human vaccine also produces an appreciable granulomatous response at the injection site (Allison & Byars (1991) Mol Immunol 28:279-284). The mode of action of an incomplete Freund's adjuvant can involve non-specific as well as specific immune responses. IFA seems to work by triggering the immunocompetent cells, which are related to the inflammatory as well as protective ability. IFA also acts as an antigen vehicle and a slow release or long-term antigen presentation device. Injecting a patient with an IFA and antigen compound, it forms a depot of antigen at the injection site, thereby protecting the antigen from degradation. From this depot the antigen is released slowly into the system and provides a prolonged antigen presentation as well as expanded total contact surface area and the attraction of inflammatory cells. Macrophages digest most of the incorporated materials and present the processed antigens on their surface.

The specific enhancing effect of the IFA on the antigen immunogenicity has been found to lead to increased humoral immunity (preferentially protective antibody production; IgG1 in humans and IgG2a in mice) and to elicit specific cell mediated immunity (preferentially Th2 type and Tregs). Specifically, human recombinant insulin B-chain in IFA results in Th2 cytokine pattern in NOD mice islets (Ramiya et al. (1996) J Autoimmun 9:349-356). IFA is unique among adjuvants tried for diabetes prevention in animal models. Ramiya and coworkers (supra) concluded that both alum and DPT as adjuvants have 'non-specific' protective effects unrelated to the antigen used, while IFA is the only one with antigen specific protective effect for diabetes prevention in animals.

IFA, preferably an IFA approved for human use, e.g., Montanide (e.g., Montanide ISA51, Seppic Inc., France) or an equivalent composition, is a preferred adjuvant for use in the methods and vaccines described herein. Montanide ISA51 has shown no systemic or significant local side effects in our animal and in our human studies.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

The compounds may be formulated for parenteral administration by injection, e.g., by bolus injection or continuous infusion. Injection (intravenous or subcutaneous) is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

In some embodiments, the combination as described herein may be administered parenterally, by injection subcutaneously, or intramuscularly. In some embodiments, a preferred mode of administration is intramuscularly. For example, the Type 1 diabetes autoantigen as described herein can be given as an intramuscular injection, preferably a deep intramuscular injection, in a small volume, e.g., 1 ml. The autoantigen can be administered once, or more than once. It can be given, for example, before, or after the onset of Type 1 diabetes mellitus.

The dosage may also depend on the route of administration and will vary according to the size of the host. For example, 2 mg of human insulin B chain solution can be administered to an adult human. The concentration of the active ingredient protein in an immunogenic composition according to the invention is in general about 1 to 95%.

A vaccine can also contain an adjuvant, e.g., an oil based adjuvant, e.g., IFA. Preferably, the vaccine contains an IFA suitable and approved for human use, e.g., Montanide ISA 51 or an equivalent composition.

The vaccines are prepared under conditions suitable for human administration. Preferably, the vaccine injection is prepared as an emulsion immediately before administration, under sterile conditions, by using high pressure sterile syringes as a 50/50 (w/w) emulsion of insulin B-chain/IFA.

The methods and vaccines described herein can be used to prevent the onset of an autoimmune disease, e.g., diabetes mellitus. The methods and vaccines can also be used to arrest the autoimmune destruction of tissue, e.g., pancreatic β-cells. The methods and vaccines are useful to arrest the autoimmune destruction, even at a late stage. For example, at the time of clinical onset of type 1 diabetes mellitus, significant number of insulin producing β-cells are destroyed but around 15% maybe as much as 40% are still capable of insulin production. If the autoimmune process can be arrested even in this late stage, these cells can be preserved. The β-cells have some limited capacity to replicate and precursors may form new β-cells.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer. Alternatively, the active ingredient may be in powder form for constitution with a suitable vehicle, e.g., sterile pyrogen-free water, before use.

The amount of the combination of a CTLA4 molecule and insulin β-chain provided to the subject will depend on both the size and weight of the subject as well as the progression of the disease. For the compounds described herein, the therapeutically effective amount can be initially determined from in vitro assays. Since the compounds of the present invention may have a low absorption and low bioavailability, the therapeutically effective amount may be determined from, for example, fecal concentration of the compounds or metabolites thereof or biomarkers from the blood. As is well known in the art, therapeutically effective amounts for use in humans can also be determined from animal models. A therapeutically effective dose can also be determined from human data for compounds which are known to exhibit similar pharmacological activities. The applied dose can be adjusted based on the relative potency of the administered compound as compared with the known compound.

Patient doses for parenteral administration of the compounds described herein, typically range from about 1 mg/day to about 10,000 mg/day, more typically from about 10 mg/day to about 1,000 mg/day or from about 250 mg/day to about 2,000 mg/day, and most typically from about 50 mg/day to about 500 mg/day or from about 0.5 mg/day to about 10 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

Both the CTLA4 molecule and the insulin B-chain may be administered in a single dose or they may be administered separately, where separate administration contemplates administration at near the same time or administration at different times, such as one in the morning and the other in the evening, or one twice a day and the other once a day. The two drugs may be given simultaneously or in different order, i.e. CTLA4-Ig first followed by insulin B-chain in IFA or insulin B-chain and then CTLA4-Ig at different timepoints.

The dosing may be over a period of time, such as once a month, or every 28 days. In some embodiments, additional doses (e.g., bolus dosing) may be given at the beginning of treatment. In some embodiments, a dose containing approximately 1, 3, 5, 10, 20, 30, 50, 100 mg/kg of the fusion protein. In some embodiments, a dose containing approximately 1, 3, 5, 10, 20, 30, 40, 50, 100, 500 microg/kg of the diabetes autoantigen.

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

As used herein, the terms "administering" or "administration" are intended to encompass all means for directly and indirectly delivering a compound to its intended site of action.

An "autoantigen" as used herein, is a protein that despite being a normal cell or tissue constituent, can be the target of a humoral or cell-mediated immune response in a subject. For example, diabetes Type 1 autoantigens are typically normal protein constituents of pancreatic cells. An "immunologically active fragment" of an autoantigen described herein is an autoantigen in which one or more amino acid residues have been deleted and the fragment retains the ability to react with immune cells or with an autoantigen antibody or to stimulate the production of antibodies against the autoantigen. For example, an immunologically active fragment can be an autoantigen polypeptide in which residues have been successively deleted from the amino- and/or carboxyl-termini, while substantially retaining immunogenic activity. For example, insulin B-chain (amino acids 25-54 of SEQ ID NO:1) is an immunologically active fragment of preproinsulin; a polypeptide that includes amino acids 33-47 of SEQ ID NO: 1 is an immunologically active fragment of B-chain; a polypeptide that includes amino acids from about 600 to 979 of SEQ ID NO:3 includes an immunologically active fragment of IA-2. In a preferred embodiment, the immunologically active fragment is a fragment of any of SEQ ID Nos: 1-6. Preferred fragments lacks one or more biological activities of the native autoantigen, but retain the ability to react with an autoantigen antibody and immune cells. E.g., a preferred insulin fragment or variant lacks a hypoglycemic effect. Preferably, an immunologically active fragment of an autoantigen described herein is between 4 and 400 amino acid residues in length, more preferably between 10 and 300 amino acid residues in length, more preferably between 30 and 200 amino acid residues in length.

The phrase "delaying the progression" as used herein in the context of delaying the progression of diabetes mellitus means that the loss of functional residual β-cell mass, after the clinical onset of Type 1 diabetes is delayed. The delayed progression of T1DM can be measured, for example, by measuring C-peptide production.

An "immunologically active variant" of an autoantigen described herein is an autoantigen that has been modified by addition, modification or substitution of one or more amino acid residues in the naturally occurring autoantigen and retains the ability to react with an autoantigen antibody or to stimulate the production of antibodies against the autoantigen. The variants described herein encompass allelic and polymorphic variants, and also muteins and fusion proteins that retain the ability to bind an autoantigen antibody or to produce an immune response against the autoantigen in a human. For example, up to 20%, preferably up to 10%, of the amino acid residues of an autoantigen can be replaced with substitute amino acids, so long as the variant retains the ability to bind autoantigen or produce an immune response against the autoantigen, e.g., in a human. A variant can also include an autoantigen or fragment thereof described herein in which one or more amino acids have been inserted or added, e.g., an autoantigen that has been coupled or fused to a carrier peptide. Also included are variants containing modifications, such as incorporation of unnatural amino acid residues, or phosphorylated, sulfonated, or biotinylated amino acid residues. Modifications of amino acid residues may also include aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Other modifications include the addition of other moieties, particularly those that may increase the immunogenicity of the autoantigen. Preferred variants lack one or more biological activities of the native autoantigen, but retain the ability to react with an autoantigen antibody or immune cells. E.g., a preferred insulin variant lacks a hypoglycemic effect.

The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's, The Science and Practice of Pharmacy, (Gennaro, A. R., ed., 19$^{th}$ edition, 1995, Mack Pub. Co.), discloses various carriers used in formulating pharmaceutical compositions and known techniques for the preparation thereof. Except insofar as any conventional carrier medium is incompatible with the compounds of provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc. Excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutical composition" refers to a composition described herein, or pharmaceutically acceptable salts thereof, with other agents such as carriers and/or excipients. Preferably, a pharmaceutical composition will have the active agent present at least 95% purity, or 98% purity, or 99% purity, or more.

As used herein, the term "subject" is a human or other animal, having a diabetes, pre-diabetes, or a predisposition to diabetes. Thus, in some embodiments the subject will be in need of the therapeutic treatment as provided herein. Preferred patients are mammals. Examples of patients include but are not limited to, humans, horses, monkeys, dogs, cats, mice, rates, cows, pigs, goats and sheep. In some embodiments, "subjects" are generally human patients having diabetes. In some embodiments, "subjects" are human patients who have been diagnosed with T1DM within the last 200, 100, or 50 days. In some embodiments, "subjects" are human patients who have been diagnosed with diabetes mellitus but still have residual beta-cell function. In some such embodiments the residual beta-cell function is detectable or at least 10%, 20%, 30%, 40%, 50%, 60%, or more of the beta cells in a fully functioning pancreas.

The term "therapeutically effective amount" refers to an amount effective, at dosages and for periods of time necessary, to achieve the desired biological or medicinal response in a cell culture, tissue system, animal, or human (e.g., the desired therapeutic result). A therapeutically effective amount of the composition may vary according to factors such as the disease state, age, sex, and weight of the individual, and the ability of the CTLA4 molecule and/or diabetes autoantigen to elicit a desired response in the individual. A therapeutically effective amount is also one in which any toxic or detrimental effects of the pharmacological agent are outweighed by the therapeutically beneficial effects. In some embodiments, the response includes alleviation and/or delay of onset of one or more symptoms of the disease, condition, or disorder being treated.

The term "treatment" or "treating" as used herein is defined as the application or administration of the therapeutic agents to a subject, or application or administration of the therapeutic agents to an isolated tissue or cell line from a subject who has diabetes, a symptom of disease or a predisposition toward a disease. Treatment is intended to encompass preventing the onset, slowing the progression, reversing or otherwise ameliorating, improve, or affect the disease, the symptoms or of disease or the predisposition toward disease. For example, treatment of a subject, e.g., a human subject, with a composition described herein, can slow, improve, or stop the ongoing autoimmunity, e.g., a reaction against pancreatic β-cells, in a subject before, during, or after the clinical onset of Type 1 diabetes.

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or within 2 standard deviations, as per the practice in the art. Alternatively, "about" can mean a range of up to 20%, preferably up to 10%, and more preferably up to 5% of a given value. Where particular values are described in the application and claims, unless otherwise stated, the term "about" meaning within an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules, "a resin" includes one or more of such different resins and reference to "the method" includes reference to equivalent steps and methods known to those of ordinary skill in the art that could be modified or substituted for the methods described herein.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto.

EXAMPLES

Aspects of the applicant's teachings may be further understood in light of the following examples, which should not be construed as limiting the scope of the applicant's teachings in any way.

Example 1

Administration of Abatacept

Patients (aged 6-45 years) diagnosed with Type 1 diabetes within the past 100 days were parallel-screened for this study. Patients were eligible to participate in the study if they had at least one diabetes-related autoantibody (microassayed insulin antibodies [if duration of insulin therapy was less than 7 days]; glutamic acid decarboxylase-65 [GAD-65] antibodies; islet-cell antigen-512 [ICA-512] antibodies; or islet-cell autoantibodies) and had stimulated C-peptide concentrations of 0.2 nmol/L or higher measured during a mixed-meal tolerance test (MMTT) done at least 21 days after diagnosis of diabetes and within 37 days of randomization.

People whose blood samples screened positive for serum antibodies to hepatitis B surface antigen, hepatitis C, or HIV were excluded from participation. Samples were also tested for Epstein-Barr virus (EBV). Individuals who had evidence of active EBV infection at the time of screening were ineligible. Participants who showed evidence of active EBV infection after randomization did not receive additional study drug until resolution.

Patients were randomly assigned in a 2:1 ratio, stratified by participating site, to receive experimental treatment with abatacept or placebo using a double blind protocol. Table 1 provides the baseline demographic and laboratory characteristics of participants

TABLE 1

| | Abatacept (n = 77) | Placebo (n = 35) |
|---|---|---|
| Age | | |
| Mean (years) | 13.9 (6.9) | 13.7 (5.3) |
| Median (years) | 12 (6-36) | 14 (7-34) |
| Men | 41 (53%) | 25 (71%) |

TABLE 1-continued

| | Abatacept (n = 77) | Placebo (n = 35) |
|---|---|---|
| Race* White | 71 (93%) | 32 (91%) |
| Ethnic origin Non-Hispanic | 67 (87%) | 31 (89%) |
| Number of diabetes-related autoantibodies† | | |
| 1 | 16 9 (12 | 4 (11%) |
| 2 | 26 (34%) | 9 (26%) |
| 3 | 26 (34%) | 15 (43%) |
| 4 | 16 (21%) | 7 (20%) |
| Number of days from diagnosis to first infusion‡ | 87.9 (14.1) | 83.2 (17.8) |
| Weight (kg) | 52.6 (21.9) | 53·0 (19/7) |
| Body-mass index (kg/m$^2$) | 21/0 (4.5) | 20.5 (3/9) |
| Mean AUC for C-peptide (nmol/L) | 0.743 (0/42) | 0.745 (0.31) |
| HbA1c at baseline* (%) | 6.31% (0.80) | 6.74% (0.94) |
| Total daily insulin dose at baseline* (U/kg) | 0.385 (0.24) | 0.339 (0.22) |
| Ketoacidosis at diagnosis | 25 (32%) | 8 (23%) |
| Diabetes-associated HLA alleles present* | | |
| DR3 and DR4 | 25 (34%) | 16 (49%) |
| DR3 only | 11 (15%) | 5 (15%) |
| DR4 only | 30 (41%) | 10 (30%) |
| Neither | 8 (11%) | 2 (6%) |

Data are n (%), mean (SD), or median (range).
AUC = area under the curve.
HbA1c = glycated haemoglobin A1c.
*Excludes participants with data missing for indicated variable (number missing: race, 1; HbA1c, 2; insulin use, 1; HLA allele status, 4).
†Islet-cell autoantibodies by immunofluorescence not tested on 16 patients (considered negative for count).
‡Range 51-108 for abatacept group and 38-107 for placebo.

Abatacept (Orencia, Bristol-Myers Squibb, Princeton, N.J., USA) was given on days 1, 14, and 28, and then every 28 days with the last dose on day 700 (total 27 doses) as a 30-min intravenous infusion at a dose of 10 mg/kg (maximum 1000 mg per dose) in a 100 mL 0.9% sodium chloride infusion. Normal saline infusion was used as placebo. Patients did not receive any premedication.

All patients received intensive diabetes management. The goal was to achieve intensive glycaemic control as recommended by the American Diabetes Association. (American Diabetes Association. *Diabetes Care* 2011; 33 (suppl 1): S11-61.) Patients used either multiple daily insulin injections or an insulin pump. Blood glucose monitoring was done by means of frequent daily blood glucose monitoring. Use of non-insulin pharmaceuticals that affect glycaemic control was not allowed.

Blood samples were analyzed centrally. C-peptide concentrations were measured from frozen plasma with a two-site immunoenzymometric assay (Tosoh Bioscience, South San Francisco, Calif., USA). Glycated haemoglobin A1c (HbA1c) was measured with ion-exchange high-performance liquid chromatography (Variant II, Bio-Rad Diagnostics, Hercules, Calif., USA). Reliability coefficients for each assay were greater than 0.99 from split duplicate samples. Biochemical autoantibodies (microassayed insulin antibodies, GAD-65 antibodies, ICA-512 antibodies) were measured with radioimmunobinding assays and islet-cell autoantibodies (ICA) with indirect immunofluorescence. A routine chemistry panel was done (Roche Diagnostics [Indianapolis, Ind., USA] Hitachi 917 Analyzer and reagents). HLA class II alleles were measured with PCR amplification and sequence-specific hybridization. β-cell function was assessed by stimulated C-peptide secretion. The prespecified primary outcome of this trial was a comparison of the area under the curve (AUC) of stimulated C-peptide response over the first 2 h of a 4-h MMTT2, done at the 24-month visit. The 4-h MMTTs were done at baseline and at 24 months; 2-h MMTTs were obtained at 3, 6, 12, and 18 months. Patients who had completed their 2-year visit MMTT were included in the primary outcome assessment. After completion of the 2-year treatment phase, participants entered a 2-year follow-up phase to continue to assess safety and efficacy, including an MMTT every 6 months. Prespecified secondary outcomes included: slope of C-peptide over time, difference between groups in incidence of loss of peak C-peptide to less than 0.2 nmol/L, differences in HbA1c and insulin dose over time, and safety. Prespecified subgroup factors included age, sex, race, baseline C-peptide, baseline insulin use, baseline HbA1c, and HLA type.

Spotfire S+8.1, a statistical analysis software, was used for all analyses. A sample size of 108 participants was planned to provide 85% power to detect a 50% increase in geometric mean C-peptide relative to the placebo group using a test at the 0.05 level (one-sided), with 10% loss to follow-up and a 2:1 allocation to treatment versus control (based on an estimated mean of 0.248 and SD of 0.179, on the transformed scale). All analyses were based on the prespecified intention to treat cohort with known measurements. Missing values were assumed to be missing at random. The p values associated with the intention-to-treat treatment comparisons of the primary and secondary endpoints are two-sided, although the design of the trial was based on a one-sided hypothesis test. Interim analysis for endpoint treatment effect was done and reported to the data and safety monitoring board once in accordance to the method of Lan and DeMets with O'Brien-Fleming boundaries. (Lan K K G, DeMets D L. *Biometrika* 1983; 70: 659-63.) The prespecified analysis method for C-peptide mean AUC, HbA1c, and total daily insulin dose was an analysis of covariance model adjusting for age, sex, and baseline value of the dependent variable, and treatment assignment. The predicted means and associated 95% confidence intervals (CIs) for each treatment group were established at the means of the other covariates. The significance levels associated with the treatment effect were from the Wald test (from the fitted model). A normalizing transformation of log(XC-Pep+1) was prespecified for C-peptide AUC mean, and normal plots of the residuals suggested that it was adequate. The C-peptide mean AUC equals the AUC divided by the 2-h interval (i.e., AUC/120). The AUC was computed using the trapezoidal rule from the timed measurements of C-peptide during the MMTT. The time to first stimulated peak C-peptide of less than 0.2 nmol/L (a level above which was associated with decreased risk of complications in Diabetes Control and Complication Trial) was analyzed with standard survival methods (Cox model and Kaplan-Meier method). Adverse event grades were analyzed with the Wilcoxon rank sum test. (Agresti A. Categorical data analysis. New York, N.Y., USA: John Wiley and Sons, 1990.) Mean rate of change of C-peptide mean AUC from 6 to 24 months was estimated with a mixed-effects model with both random intercept and slope adjusting for age, sex, baseline C-peptide mean AUC, and treatment assignment. The initial fit included a fixed interaction effect of treatment and time, but was removed because of the absence of any statistical evidence of it being other than zero. To assess the treatment effect over the entire time period, we fitted a similar mixed model to the data with the differences that we defined time without structure and grouped by 6-month intervals.

Of the 112 patients enrolled in the study, 77 were randomly assigned to receive experimental treatment with abatacept and 35 were assigned to receive placebo. Table 1 summarizes the baseline characteristics of the two groups. The only noteworthy imbalances were the greater proportion of men in the placebo group than in the abatacept group and higher mean HbA1c in the placebo group. The number of infusions actually administered by treatment group were compared using a Wilcoxon rank sum test; no significant difference was detected (p=0.61). Overall, 2514 (83%) of 3024 potential infusions were given, and many that were not given were per protocol (e.g., patient developed EBV infection or became pregnant). 689 (93%) of 738 expected MMTTs were done. In the primary analysis at 2 years, participants assigned to abatacept had a geometric mean stimulated C-peptide 2-h AUC of 0.375 nmol/L (95% CI 0.290-0.465) versus 0.266 nmol/L (0.171-0.368) for those assigned to placebo. The adjusted population C-peptide mean 2-h AUC at 2 years was 0.378 nmol/L for the abatacept group and 0.238 nmol/L for the placebo group; thus, C-peptide AUC at 2 years was 59% (95% CI 6.1-112) higher with abatacept (p=0.0029). The result remained unchanged and significant (p=0.0028) when baseline HbA1c was added as a covariate. To address the difference in C-peptide concentrations from baseline to the 2-year assessments (primary endpoint), C-peptide results for 3, 6, 12, and 18 months were separately modeled.

Figure 2:
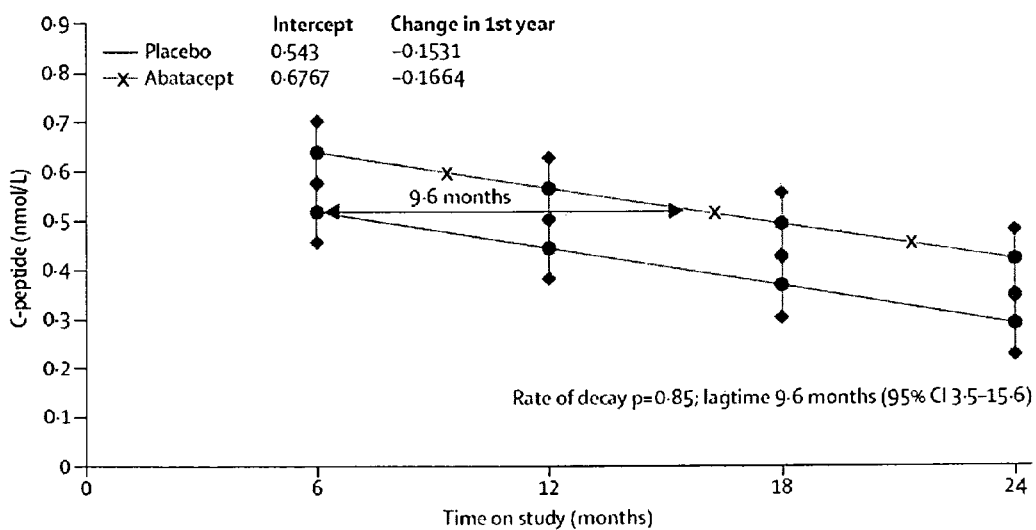
FIG. 2 is the predicted population mean of stimulated C-peptide 2-h AUC mean over time for each treatment group. Estimates are from the analysis of mixed-effects model adjusting for age, sex, baseline value of C-peptide, and treatment assignment, and including a fixed effect for time as a linear line on the log(y+1) scale. AUC=area under the curve.
Figure 3:
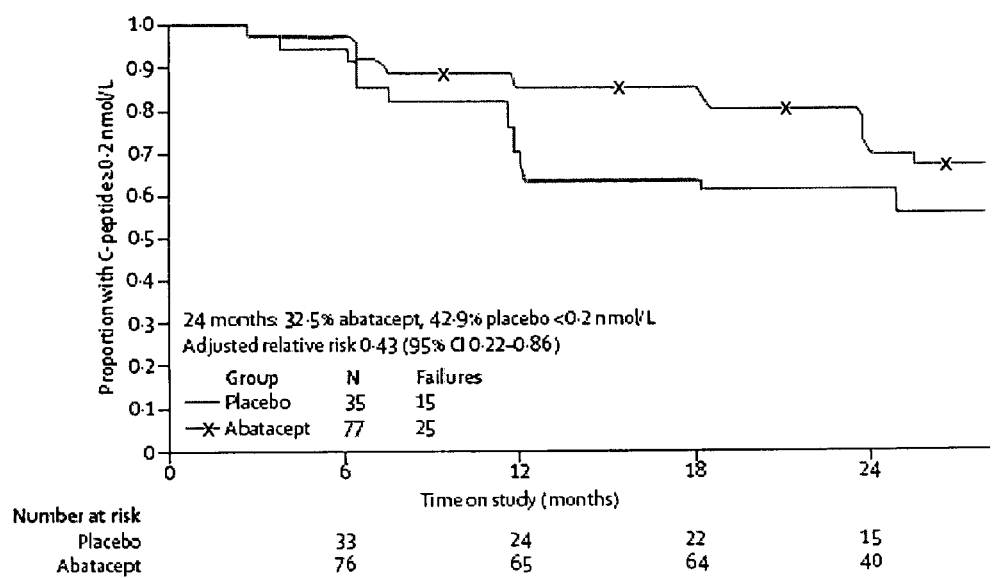
FIG. 3 is the proportion of participants with 2-h peak C-peptide remaining at or above 0.2 nmol/L over time for each treatment group.
Figures 4A, 4B:
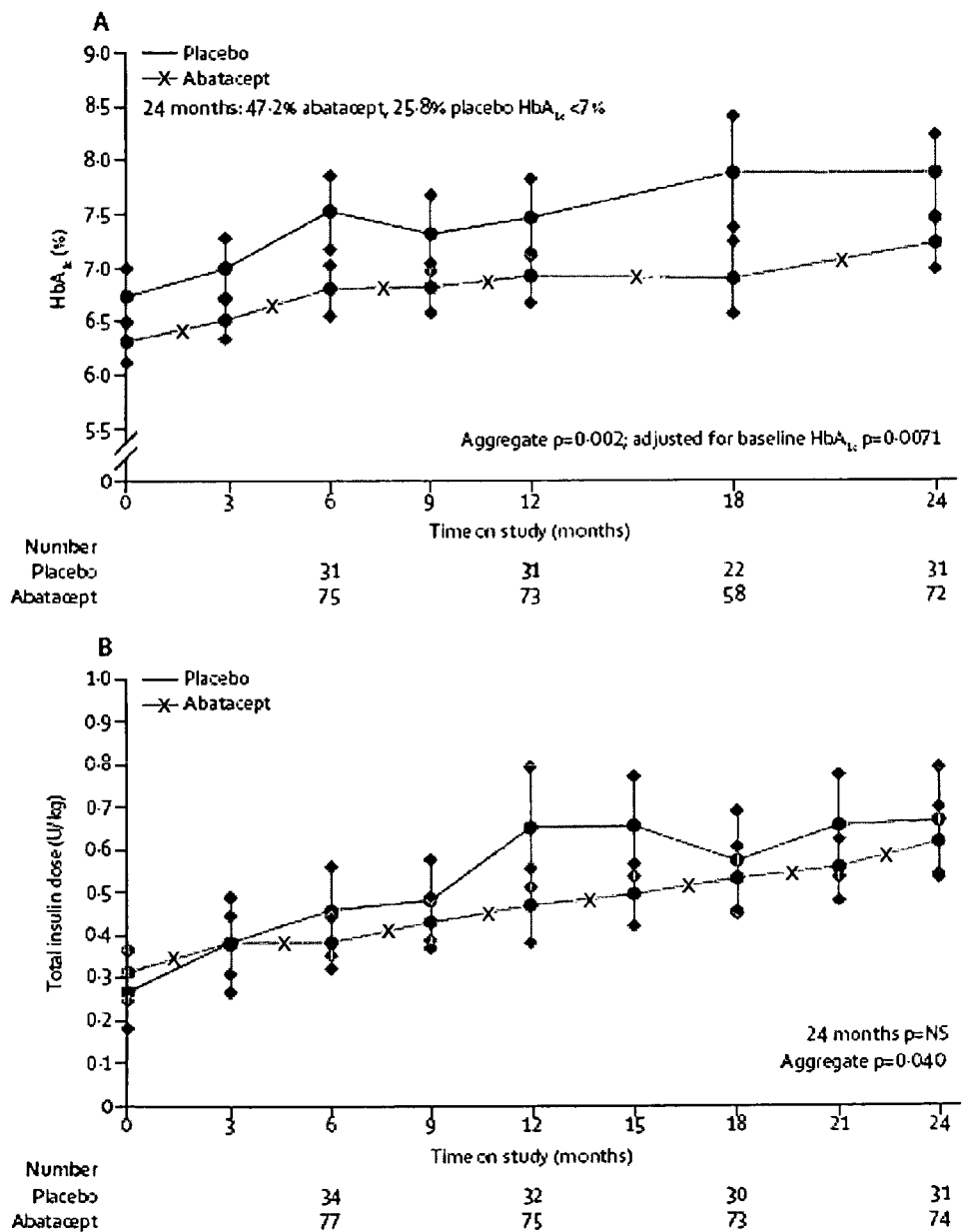
FIGS. 4A and 4B are the population mean of (A) HbA1c and (B) insulin use over time for each treatment group. Estimates are from the ANCOVA model adjusting for age, sex, baseline value of HbA1c, and treatment assignment. Insulin use is per kg of bodyweight, at 3-month intervals. Error bars show 95% CIs. HbA1c is glycated haemoglobin A1c.

FIG. 1 shows the adjusted population C-peptide mean 2-h AUC over 2 years. Patients who received abatacept had a significantly higher mean AUC at 6, 12, and 18 months than did those assigned to placebo, and over all time points in aggregate (p=0.0022). To calculate the effect of treatment on delaying the reduction of C-peptide, we calculated the predicted population mean of C-peptide AUC mean by treatment group over time (FIG. 2). The lines are based on the fitting of a mixed linear model using all available data from MMTTs at 6, 12, 18, and 24 months. When testing for the improvement in the fit for the interaction term of slope and treatment (i.e., testing the evidence that the two treatment groups had differing C-peptide decay rates), this result was not significant (p=0.85). Consequently, a simpler model assuming identical slopes was used and FIG. 2 shows these results. Thus, estimated lag time in the means of the abatacept group to drop to the same level as those of the placebo group was 9.6 months (95% CI 3.47-15.6). By the 24-month assessment, (32%) patients in the abatacept group had an AUC peak stimulated C-peptide less than 0.2 nmol/L, compared with 15 (43%) patients on placebo (FIG. 3). The adjusted relative (abatacept to placebo groups) risk of peak C-peptide falling below 0.2 nmol/L was 0.433 (95% CI 0.218-0.861). During the 24 months of follow-up, the abatacept group had a lower adjusted mean HbA1c (FIG. 4) than did the placebo group (for all time points in the aggregate, p=0.002), although HbA1c was also lower at baseline. Nonetheless, even after adjustment for the difference at baseline, the treatment group difference over 24 months persists (p=0.0071). At study end, 34 (47%) patients on abatacept had HbA1c lower than 7% compared with eight (26%) on placebo. This is particularly noteworthy as 86% of all patients were under 18 years of age; in this group this HbA1c is better that the ADA age-specific target HbA1c. Participants in the abatacept group had lower insulin doses at some time points (6 and 12 months) during the study, but at 24 months, insulin doses in the two groups were similar (FIG. 4; p=NS at 24 months, but because of differences at the earlier time points, p=0.040 for all time points in the aggregate).

Figure 5:
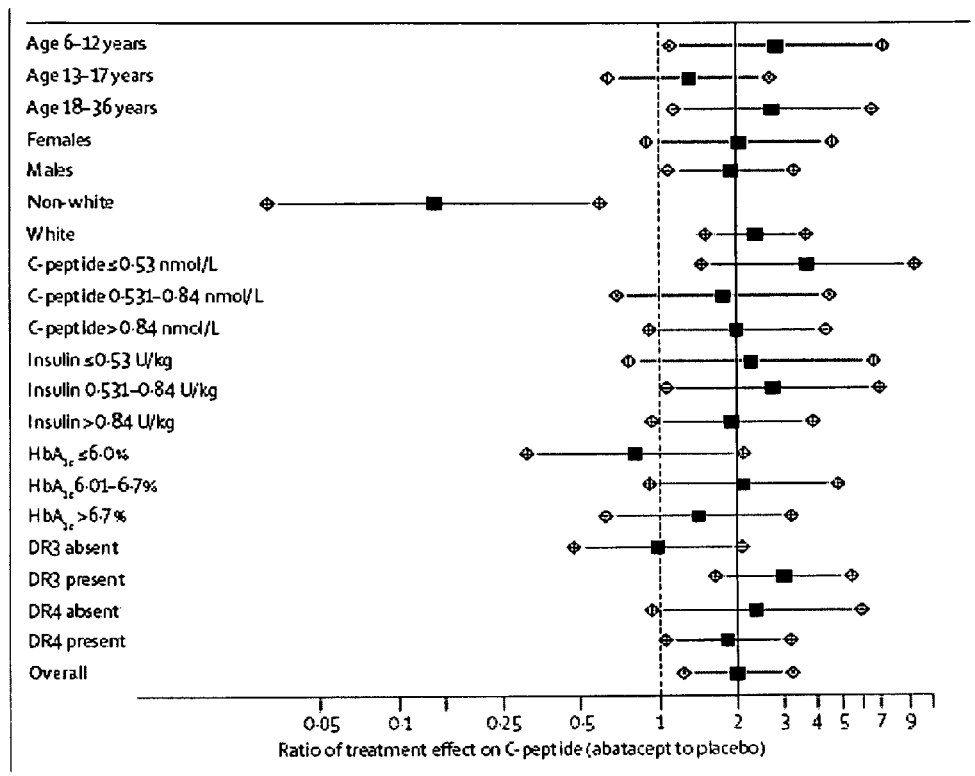
FIG. 5 is the ratio (abatacept to placebo) of treatment effect on 2-year stimulated C-peptide AUC mean within categories of prespecified baseline factors. Estimates are from the ANCOVA modeling log of C-peptide adjusting for age, sex, baseline value of C-peptide, the indicated categorized factor, treatment assignment, and treatment interaction terms. The homogeneity test of treatment effect was significant for DR3 allele status (p=0.025) and race (p=0.0003). AUC=area under the curve. HbA1c=glycated haemoglobin A1c.

FIG. 5 shows the results of a homogeneity test of treatment effect on age, sex, race, baseline C-peptide, baseline insulin use, baseline HbA1c, and HLA type. The apparent adverse effect of abatacept in non-white participants might be hypothesis-generating, however the groups size was small.

Table 2 and Table 3 summarize safety and adverse events. Abatacept was well tolerated. Infusion-related adverse events occurred with low frequency (47 of 2514 infusions [2%] involving 27 patients) and were not clinically significant. Of these, 36 reactions occurred in 17 (22%) of 77 patients on abatacept and 11 reactions in six (17%) of 35 patients on placebo (p=0.62 for proportion of participants by Fisher's exact test). Overall adverse event rate (including laboratory abnormalities) was low with no difference between the two groups. Specifically, there was no increase in infection (including EBV) or in neutropenia (which occurred in seven [9%] of patients on abatacept, five [14%] on placebo). There were seven episodes of hypoglycemia reported as an adverse event, two of which were severe hypoglycemia (one in each group).

TABLE 2

Number of patients by worst grade of adverse effects

|  | Abatacept (n = 77) | Placebo (n = 35) |
| --- | --- | --- |
| None | 14 (18%) | 8 (23%) |
| Grade 1 | 1 (1%) | 1 (3%) |
| Grade 2 | 44 (57%) | 17 (49%) |
| Grade 3 | 12 (16%) | 7 (20%) |
| Grade 4 | 5 (6%) | 2 (6%) |
| Grade 5 1 | (1%)* | 0 |

Data are n (%). Worst grade by treatment group was not statistically different with a Wilcoxon Rank Sum Test.
*Accidental death, unrelated to study.

TABLE 3

Number of events and patients by type of adverse event

|  | Abatacept (n = 77) Number of events | Placebo (n = 35) Number of patients with events | Abatacept (n = 77) Number of events | Placebo (n = 35) Number of patients with events |
| --- | --- | --- | --- | --- |
| Allergy/immunology | 3 | 2 (3%) | 0 | 0 |
| Auditory/ear | 3 | 3 (4%) | 0 | 0 |
| Blood/bone marrow | 16 | 11 (14%) | 18 | 6 (17%) |
| Cardiac arrhythmia | 1 | 1 (1%) | 1 | 1 (3%) |
| Cardiac, general | 2 | 2 (3%) | 0 | 0 |
| Constitutional symptoms | 19 | 15 (19%) | 2 | 2 (6%) |
| Death* | 1 | 1 (1%) | 0 | 0 |
| Dermatology/skin | 15 | 13 (17%) | 5 | 4 (11%) |
| Endocrine | 4 | 4 (5%) | 2 | 2 (6%) |
| Gastrointestinal | 30 | 18 (23%) | 11 | 7 (20%) |
| Infection | 63 | 32 (42%) | 31 | 15 (43%) |
| Hypoglycaemia | 5 | 3 (4%) | 2 | 1 (3%) |
| Metabolic/laboratory† | 8 | 6 (8%) | 4 | 2 (6%) |
| Musculoskeletal/soft tissue | 13 | 11 (14%) | 7 | 6 (17%) |
| Neurology | 13 | 8 (10%) | 3 | 2 (6%) |
| Ocular/visual | 3 | 3 (4%) | 1 | 1 (3%) |
| Pain | 7 | 6 (8%) | 5 | 4 (11%) |
| Pulmonary/upper respiratory | 20 | 10 (13%) | 7 | 4 (11%) |
| Renal/genitourinary | 0 | 0 | 1 | 1 (3%) |
| Secondary malignancy | 1 | 1 (1%) | 0 | 0 |
| Sexual/reproductive function | 1 | 1 (1%) | 0 | 0 |
| Surgery/intraoperative injury | 2 | 2 (3%) | 0 | 0 |
| Syndromes | 9 | 9 (12%) | 5 | 5 (14%) |
| Total | 239 |  | 105 |  |

Data are n or n (%). Adverse effect category by treatment group was tested with a one-sided (alternative of higher frequency in abatacept group) Fisher's Exact Test; only constitutional symptoms were significant (p = 0·049).
*Accidental death, unrelated to study.
†Other than hypoglycaemia.

Results show that over 2 years co-stimulation modulation with abatacept slows the reduction in β-cell function in recent-onset Type 1 diabetes by 9.6 months. The early beneficial effect suggests that T-cell activation still occurs around the time of clinical diagnosis of Type 1 diabetes, even though the disease course has presumably been in progress for several years. However, despite continued administration of abatacept over 24 months, the fall in β-cell function in the abatacept group parallels that in the placebo group on the basis of the mixed-model results that included the time interval from 6 to 24 months. This subsequent reduction in β-cell function causes us to speculate that continuing T-cell activation subsides as the clinical course of the disease progresses. Nevertheless, the difference from the placebo group is maintained during drug administration. Further observation will establish whether the beneficial effect continues after cessation of monthly abatacept infusions. Follow up of these patient shows that the drug beneficial effect lasts beyond the drug administration for at least one year.

Abatacept was well tolerated, with no difference between the two groups in adverse events. However, a potential limitation to clinical applicability is that live vaccines cannot be used within 3 months of abatacept treatment. This factor might be important in view of the young age of the target population. The main effect seems to occur early after initiation of treatment with subsequent resumption of the fall in β-cell function. This pattern is reminiscent of the effects of anti-CD3, anti-CD20, and a GAD-65 vaccine, all of which showed some efficacy followed later by a reduction in β-cell function parallel to that in the control group. However this approach stands out as this has little or no appreciable side effects unlike the other interventions enlisted. This finding is consistent with our notion that there is an early window of opportunity after diagnosis in which T-cell activation is prominent. The 59% higher mean AUC C-peptide with abatacept than with placebo at 24 months in our study is similar to that seen with those other interventions, although direct comparison of studies is difficult because of differences in important baseline characteristics, including age, disease duration at time of randomization, and baseline HbA1c. Moreover, our study differs from those studies in that abatacept was administered continuously throughout the study, whereas in the case of anti-CD3, anti-CD20, and GAD-65 vaccine, administration of drug was completed within 2-4 weeks after randomization. Crucially, our study was not designed to establish whether a short treatment protocol would be sufficient to maintain improved C-peptide secretion over 2 years or whether a continuation of treatment is needed beyond 2 years. With all patients having completed their course of abatacept, the ongoing follow-up phase of the study will investigate whether the improved C-peptide secretion is sustained after discontinuation of the drug and for how long. Long-term follow-up of patients in one anti-CD3 trial showed diminishing difference in C-peptide secretion between the treated and the placebo group after 3 years. This is not the case for abatacept as the data one year off treatment shows that the beneficial effect is maintained, the difference in C-peptide preservation between the abatacept treated and the placebo group has not diminished (the abatacept group has 62% more C-peptide than the placebo group at 3 years).

In the abatacept group, mean HbA1c was lower than that in the placebo group throughout the trial, although it was also lower at baseline. The maintenance of HbA1c lower than 7% for 18 months in the abatacept-treated group is noteworthy because 96 (86%) study participants were 18 years or younger. The clinical importance of HbA1c at this level has been well documented. (The Diabetes Control and Complications Trial Research Group. *N Engl. J Med* 1993; 329: 977-86.) Insulin use was similar in the two groups and thus did not contribute to the difference in HbA1c. In our trial, abatacept-treated patients with recent-onset Type 1 diabetes had more endogenous insulin production, measured by C-peptide, during the 2 years of study drug administration. The duration of these effects after discontinuation of abatacept is being tested in ongoing follow-up of these patients. The one-year-off-therapy data shows that the beneficial effects of abatacept persist at least for one year beyond drug administration, including significantly better HbA1c at 3 years in the abatacept group. The patients are being followed further. Abatacept administered over 2 years showed an excellent safety profile in patients with Type 1 diabetes. Its main effect seems to occur early after the initiation of treatment, however further studies are needed to test how far in the autoimmune process this drug can be effective in slowing down the autoimmunity. These approaches might be more easily tested with a subcutaneous version of abatacept.

Example 2

Preparation of Insulin B-Chain

Human insulin was made by standard solid-phase peptide synthesis (SPPS) procedure, described herein and in U.S. Pat. Pub. 2006/0183670, herein incorporated by reference. The assembly strategy used in the protein synthesis was ABI (Applied Biosystem Inc.)-Fmoc/Thr. The Fmoc group protects the α-amino group of the amino acid. The peptide was assembled from the C-terminal towards the N-terminal with the α-carboxyl group of the starting amino acid attached to a solid support (resin). The resin used for assembly was polystyrene bead, an insoluble support with size of 400-1000 micron in diameter swelled after washing with NMP (N-methylpyrrolidone). The resin was preloaded with the first amino acid (Thr) from the C-terminal.

The two steps were chain assembly and purification under sterile conditions.

The first step in chain assembly is deprotection, or removal of the protecting group The Fmoc protecting group is removed by 22% piperidine. Conductimetric feedback of carbamate salt formed via removal of Fmoc group with piperidine/NMP showed the coupling efficacy. After deprotection, the next amino acid is activated and coupled to the deprotected amino end of the growing peptide and forms the peptide bond. Activation of the incoming amino acid carboxyl group was achieved by HBTU/HOBt. Between couplings, the column was washed with methanol and NMP (N-methylpyrrolidone), which swells the resin and washes out residues.

The cycle was repeated until a peptide of desired length was achieved. A wash step was performed with DCM (dichloromethane), which removes NMP from the resin, followed by thorough washing with highly volatile methanol, an easily removable solvent which evaporates and dries.

Cleavage from the resin and removal of side-chain protecting groups. A cleavage mixture was prepared (0.75 g crystalline phenol+0.25 g ethanedithiol+0.5 ml thioanisol+0.5 ml deionized $H_2O$+10 ml trifluoroacetic acid). The dried peptide-resin was incubated in cool flask in ice bath (10 ml mixture/100-150 mg peptide-resin) for 1.5 h. Then the peptide was isolated from the reaction mixture by glass funnel filtration under high vacuum. The peptide was precipitated with cold methyl t-butyl ether (MTBE) and vacuum dried.

The purification step under sterile conditions was performed with reverse phase HPLC. Buffer A=0.1% trifluoroacetic acid (TFA) and buffer B=70% acetonitrile, 30% $H_2O$, 0.09% trifluoroacetic acid (TFA). By using a C18 column, the elution of the sample was based upon hydrophobicity (hydrophilic sample elutes earlier). The peak detection was performed by absorbance measurement of peptide bond at 214 nm and identified by mass spectrometry. The desired fraction was pooled in sterile vials and lyophilized with sample taken for AAA (amino acid analysis) analytical rpHPLC and Mass Spectrometry.

The results of quality control tests on the B-chain produced provide a clear solution with a pH of 3.5 to 4.5 and a protein concentration of 3.5-4.5 mg/ml (3.82 mg/ml) measured using Bio-Rad Assay Bio-Rad Laboratories. The immunoreactivity/potency of human insulin RIA was 10-30 uU/mg protein/ml (80.2 uU/ml) using Diagnostic System Laboratorieskit. Purity was measured using HPLC to provide an area p % of at least 95% (>99%) corresponding to <500 ppm (<20 ppm). The identity of the B-chain was verified using mass spectrometry to provide a mass of 3400-3450 Da (single major peak 3428.7 Da). The amino acid sequence analyzer provided 30 amino acid of human B-chain insulin sequence. Pyrogens were measured via the standard USP method and meet requirements for absence of absence of pyrogens. Sterility for the absence of pyrogens was also measured and the peptide was found to be sterile.

The insulin B-chain can be treated to increase its solubility, e.g., to counter the effect of its hydrophobicity. This can be done by acidification and/or by using 4M urea buffer and/or by reducing cysteine with DTT to avoid dimerization.

Example 3

Administration of Insulin B-Chain

The diabetes prone BBDP/WOR rats (the only other animal model of Type 1 diabetes apart from the NOD mice) received the IBC (insulin B-chain in IFA) vaccine at a diabetes and insulitis free period of their life and neither the low dose nor the high dose precipitated early insulitis or diabetes.

Serum samples from the BBDP/WOR rats (6 rats/groups) were analyzed for insulin antibodies. There was a significant difference between the vehicle control vs. 100 μg insulin B-chain/rat and 500 μg insulin B-chain/rat doses (23.6 μU/ml+3.9SE vs. 37.9 μU/ml+4.5SE and 44.5 μU/ml+3.3SE; significance p=0.03 and p=0.002 respectively; no significant difference between low and high dose groups in insulin antibody titers). The IBC vaccine was prepared fresh before injecting the animals. The preparations were sampled on Day 1 and Day 14.

The insulin B-chain was also analyzed for pyrogens as per the standard USP method and been reported as meeting the requirements for absence of pyrogens.

IFA approved for human use has been used, thus these intervention strategies can be directly applied in human diabetes. The IFA is safe and effective in humans. IFA is currently used in HIV and other vaccination trials (peptide-based melanoma vaccine at Univ. Virginia) approved by FDA. Potential local side effects are similar to any commonly used adjuvant vaccinations (alum is currently used in human vaccines) and can include induration, moderate pain and low-grade fever. The injections can be given in small volume (1 ml) in deep intramuscular space, thus minimizing the local side effects.

The composition contains two components: an adjuvant, and insulin B-chain and was prepared under conditions suitable for human administration. The first component is insulin B-chain, prepared and solubilized as described in Example 2.

The second component is an IFA, e.g., Montanide ISA51 (Seppic Inc. France; Drug Master-file No: 10870DMF) or an equivalent composition. This IFA has been used in our animal studies and showed no systemic or significant local side effect. The injections were prepared fresh, immediately before administration, as an emulsion, in a lamina-flow protected hood, under sterile conditions by using high pressure sterile syringes with an 18 gauge spatial connector. 2 mg of insulin B-chain (0.5 ml) was mixed with Montanide ISA51 (0.5 ml). An equivalent composition can be used. The emulsion is a 50/50 (weight by weight) emulsion. The emulsion was given intramuscularly to an adult human subject in a 1 ml volume in the thigh.

A comprehensive toxicology/safety study on the vaccine described herein was performed. Intramuscular injection of the insulin B-chain/IFA vaccine on each of days 1, 7 and 14 to male BBDP/WOR and Sprague-Dawley rats at dose levels of 100 and 500 µg/rat, followed by a 14 day observation period had no toxicologically significant effects on clinical observation, body weights, food consumption, clinical pathology (hematology, coagulation, and clinical chemistry) and organ weights. Macroscopic (all animals) and microscopic (BBDP/WOR rats in low dose, high dose and vehicle control groups) evaluation showed injection site changes, including granulomatous inflammation attributable to the vehicle article.

Example 4

Combination Pre-Clinical Study

The CTLA4-Ig with human insulin B-chain vaccine combination therapy in fully diabetic NOD mice was not seen to reverse the diabetes in these animals. Thus, the combination therapy did not cure the already diabetic NOD mice. Since it has previously been observed that only massive immune suppression like antiCD3 cure a population of the NOD from diabetes-, such a result is not surprising. However the survival was better in the combination therapy starting with abatacept followed by B-chain vaccine, than in either abatacept or B-chain vaccine alone, thus providing a clinically useful effect. The diabetes in NOD is florid autoimmune process compared to diabetes in human. Abatacept alone given to NOD mice shortly before their onset of diabetes (>10 weeks of age; Lenschow et al.) did not alter the course of the disease in these animals, however abatacept alone was hugely effective in human even after the clinical onset of their diabetes. Thus abatacept did not cure NOD diabetes in this study has low relevance to a finding that the combination as described herein can be hugely effective in human disease even in an advanced stage i.e. post clinical onset. Thus treatment effect is expected before, at or after clinical diagnosis in humans (longer survival in NOD means that their self insulin production lasted longer) both in the human prevention and intervention settings. (See *Clin Immunol.* 2012 March; 142(3): 402-3).

Example 5

Human Trial

Human insulin B-chain in IFA (Montanide ICA 51) was given to newly diagnosed patients with Type 1 diabetes in a phase 1 safety clinical trial. In a placebo controlled double blind trial subjects received 2 mg human insulin B-chain in IFA or vehicle in IFA as a single i.m. injection within 3 months of diagnosis. The patients were followed for 2 years. The vaccination showed excellent safety profile. The vaccine induced a highly desirable immune effect, generated insulin B-chain specific regulatory T cells. Antigen specific regulatory T cells are considered the "holy grail" to control and suppress autoimmunity. Further details of this study are found in Orban et al., J. Autoimmune 2010 June; 34(4):408-15, herein incorporated by reference.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. A method of treating diabetes mellitus in a subject comprising administering to the subject:
   a cytotoxic T-lymphocyte-associated antigen 4 (CTLA4) fusion protein in a pharmaceutically acceptable carrier, and
   preproinsulin in a pharmaceutically acceptable carrier.

2. The method of claim 1, wherein said CTLA4 fusion protein is abatacept.

3. The method of claim 1, wherein said preproinsulin comprises amino acids 33-47 of SEQ ID NO:1.

4. The method of claim 1, wherein said pharmaceutically acceptable carrier is an oil-based carrier.

5. The method of claim 4, wherein said oil-based carrier is IFA or Montanide ISA.

* * * * *

```
SEQUENCE LISTING

<160> NUMBER OF SEQ ID NOS: 6

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30
```

```
Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
<213> ORGANISM: Homo sapiens

<400> SEQUENCE: 2

Met Ala Ser Pro Gly Ser Gly Phe Trp Ser Phe Gly Ser Glu Asp Gly
 1               5                  10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300
```

```
Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
            325                 330                 335

Gly Thr Thr Val Tyr Gly Ala Phe Asp Pro Leu Leu Ala Val Ala Asp
        340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
            405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
            485                 490                 495

Gly Lys Pro Gln His Thr Asn Val Cys Phe Trp Tyr Ile Pro Pro Ser
        500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
            565                 570                 575

Glu Ile Glu Arg Leu Gly Gln Asp Leu
580                 585
```

<210> SEQ ID NO 3
<211> LENGTH: 979
<212> TYPE: PRT
<213> ORGANISM: Homo sapiens

<400> SEQUENCE: 3

```
Met Arg Arg Pro Arg Arg Pro Gly Gly Leu Gly Gly Ser Gly Gly Leu
1               5                   10                  15

Arg Leu Leu Leu Cys Leu Leu Leu Ser Ser Arg Pro Gly Gly Cys
            20                  25                  30

Ser Ala Val Ser Ala His Gly Cys Leu Phe Asp Arg Arg Leu Cys Ser
        35                  40                  45

His Leu Glu Val Cys Ile Gln Asp Gly Leu Phe Gly Gln Cys Gln Val
    50                  55                  60

Gly Val Gly Gln Ala Arg Pro Leu Leu Gln Val Thr Ser Pro Val Leu
65                  70                  75                  80

Gln Arg Leu Gln Gly Val Leu Arg Gln Leu Met Ser Gln Gly Leu Ser
            85                  90                  95
```

```
Trp His Asp Asp Leu Thr Gln Tyr Val Ile Ser Gln Glu Met Glu Arg
                100                 105                 110

Ile Pro Arg Leu Arg Pro Pro Glu Pro Arg Pro Arg Asp Arg Ser Gly
            115                 120                 125

Leu Ala Pro Lys Arg Pro Gly Pro Ala Gly Glu Leu Leu Leu Gln Asp
130                 135                 140

Ile Pro Thr Gly Ser Ala Pro Ala Gln His Arg Leu Pro Gln Pro
145                 150                 155                 160

Pro Val Gly Lys Gly Gly Ala Gly Ala Ser Ser Leu Ser Pro Leu
                165                 170                 175

Gln Ala Glu Leu Leu Pro Leu Leu Glu His Leu Leu Leu Pro Pro
            180                 185                 190

Gln Pro Pro His Pro Ser Leu Ser Tyr Glu Pro Ala Leu Leu Gln Pro
            195                 200                 205

Tyr Leu Phe His Gln Phe Gly Ser Arg Asp Gly Ser Arg Val Ser Glu
    210                 215                 220

Gly Ser Pro Gly Met Val Ser Val Gly Pro Leu Pro Lys Ala Glu Ala
225                 230                 235                 240

Pro Ala Leu Phe Ser Arg Thr Ala Ser Lys Gly Ile Phe Gly Asp His
                245                 250                 255

Pro Gly His Ser Tyr Gly Asp Leu Pro Gly Pro Ser Pro Ala Gln Leu
            260                 265                 270

Phe Gln Asp Ser Gly Leu Leu Tyr Leu Ala Gln Glu Leu Pro Ala Pro
        275                 280                 285

Ser Arg Ala Arg Val Pro Arg Leu Pro Glu Gln Gly Ser Ser Ser Arg
    290                 295                 300

Ala Glu Asp Ser Pro Glu Gly Tyr Glu Lys Glu Gly Leu Gly Asp Arg
305                 310                 315                 320

Gly Glu Lys Pro Ala Ser Pro Ala Val Gln Pro Asp Ala Ala Leu Gln
                325                 330                 335

Arg Leu Ala Ala Val Leu Ala Gly Tyr Gly Val Glu Leu Arg Gln Leu
            340                 345                 350

Thr Pro Glu Gln Leu Ser Thr Leu Leu Thr Leu Leu Gln Leu Leu Pro
        355                 360                 365

Lys Gly Ala Gly Pro Asn Pro Gly Gly Val Val Asn Val Gly Ala Asp
    370                 375                 380

Ile Lys Lys Thr Met Glu Gly Pro Val Glu Gly Arg Asp Thr Ala Glu
385                 390                 395                 400

Leu Pro Ala Arg Thr Ser Pro Met Pro Gly His Pro Thr Ala Ser Pro
                405                 410                 415

Thr Ser Ser Glu Val Gln Gln Val Pro Ser Pro Val Ser Ser Glu Pro
            420                 425                 430

Pro Lys Ala Ala Arg Pro Pro Val Thr Pro Val Leu Glu Lys Lys
        435                 440                 445

Ser Pro Leu Gly Gln Ser Gln Pro Thr Val Ala Gly Gln Pro Ser Ala
    450                 455                 460

Arg Pro Ala Ala Glu Glu Tyr Gly Tyr Ile Val Thr Asp Gln Lys Pro
465                 470                 475                 480

Leu Ser Leu Ala Ala Gly Val Lys Leu Leu Glu Ile Leu Ala Glu His
                485                 490                 495

Val His Met Ser Ser Gly Ser Phe Ile Asn Ile Ser Val Val Gly Pro
            500                 505                 510

Ala Leu Thr Phe Arg Ile Arg His Asn Glu Gln Asn Leu Ser Leu Ala
        515                 520                 525
```

```
Asp Val Thr Gln Gln Ala Gly Leu Val Lys Ser Glu Leu Glu Ala Gln
    530                 535                 540

Thr Gly Leu Gln Ile Leu Gln Thr Gly Val Gly Gln Arg Glu Glu Ala
545                 550                 555                 560

Ala Ala Val Leu Pro Gln Thr Ala His Ser Thr Ser Pro Met Arg Ser
                565                 570                 575

Val Leu Leu Thr Leu Val Ala Leu Ala Gly Val Ala Gly Leu Leu Val
            580                 585                 590

Ala Leu Ala Val Ala Leu Cys Val Arg Gln His Ala Arg Gln Gln Asp
        595                 600                 605

Lys Glu Arg Leu Ala Ala Leu Gly Pro Glu Gly Ala His Gly Asp Thr
    610                 615                 620

Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
                645                 650                 655

Val Ser Ser Gln Phe Ser Asp Ala Ala Gln Ala Ser Pro Ser Ser His
            660                 665                 670

Ser Ser Thr Pro Ser Trp Cys Glu Glu Pro Ala Gln Ala Asn Met Asp
        675                 680                 685

Ile Ser Thr Gly His Met Ile Leu Ala Tyr Met Glu Asp His Leu Arg
    690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
                725                 730                 735

Lys Asn Arg His Pro Asp Phe Leu Pro Tyr Asp His Ala Arg Ile Lys
            740                 745                 750

Leu Lys Val Glu Ser Ser Pro Ser Arg Ser Asp Tyr Ile Asn Ala Ser
        755                 760                 765

Pro Ile Ile Glu His Asp Pro Arg Met Pro Ala Tyr Ile Ala Thr Gln
    770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
            820                 825                 830

His Val Tyr Glu Val Asn Leu Val Ser Glu His Ile Trp Cys Glu Asp
        835                 840                 845

Phe Leu Val Arg Ser Phe Tyr Leu Lys Asn Val Gln Thr Gln Glu Thr
    850                 855                 860

Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Arg Lys Val Asn Lys
                885                 890                 895

Cys Tyr Arg Gly Arg Ser Cys Pro Ile Ile Val His Cys Ser Asp Gly
            900                 905                 910

Ala Gly Arg Thr Gly Thr Tyr Ile Leu Ile Asp Met Val Leu Asn Arg
        915                 920                 925

Met Ala Lys Gly Val Lys Glu Ile Asp Ile Ala Ala Thr Leu Glu His
    930                 935                 940

Val Arg Asp Gln Arg Pro Gly Leu Val Arg Ser Lys Asp Gln Phe Glu
945                 950                 955                 960
```

```
Phe Ala Leu Thr Ala Val Ala Glu Glu Val Asn Ala Ile Leu Lys Ala
                965                 970                 975
Leu Pro Gln

<210> SEQ ID NO 4
<211> LENGTH: 622
<212> TYPE: PRT
<213> ORGANISM: Homo sapiens

<400> SEQUENCE: 4

Met Ser Met Arg Ser Pro Ile Ser Ala Gln Leu Ala Leu Asp Gly Val
1               5                   10                  15

Gly Thr Met Val Asn Cys Thr Ile Lys Ser Glu Lys Lys Glu Pro
                20                  25                  30

Cys His Glu Ala Pro Gln Gly Ser Ala Thr Ala Ala Glu Pro Gln Pro
                35                  40                  45

Gly Asp Pro Ala Arg Ala Ser Gln Asp Ser Ala Asp Pro Gln Ala Pro
            50                  55                  60

Ala Gln Gly Asn Phe Arg Gly Ser Trp Asp Cys Ser Ser Pro Glu Gly
65              70                  75                  80

Asn Gly Ser Pro Glu Pro Lys Arg Pro Gly Ala Ser Glu Ala Ala Ser
                85                  90                  95

Gly Ser Gln Glu Lys Leu Asp Phe Asn Arg Asn Leu Lys Glu Val Val
                100                 105                 110

Pro Ala Ile Glu Lys Leu Leu Ser Ser Asp Trp Lys Glu Arg Phe Leu
                115                 120                 125

Gly Arg Asn Ser Met Glu Ala Lys Asp Val Lys Gly Thr Gln Glu Ser
                130                 135                 140

Leu Ala Glu Lys Glu Leu Gln Leu Leu Val Met Ile His Gln Leu Ser
145                 150                 155                 160

Thr Leu Arg Asp Gln Leu Leu Thr Ala His Ser Glu Gln Lys Asn Met
                165                 170                 175

Ala Ala Met Leu Phe Glu Lys Gln Gln Gln Met Glu Leu Ala Arg
                180                 185                 190

Gln Gln Gln Glu Gln Ile Ala Lys Gln Gln Gln Leu Ile Gln Gln
                195                 200                 205

Gln His Lys Ile Asn Leu Leu Gln Gln Gln Ile Gln Val Asn Asn
                210                 215                 220

Pro Tyr Val Met Ile Pro Ala Phe Pro Pro Ser His Gln Pro Leu Pro
225                 230                 235                 240

Val Thr Pro Asp Ser Gln Leu Ala Leu Pro Ile Gln Pro Ile Pro Cys
                245                 250                 255

Lys Pro Val Glu Tyr Pro Leu Gln Leu Leu His Ser Pro Pro Ala Pro
                260                 265                 270

Val Val Lys Arg Pro Gly Ala Met Ala Thr His His Pro Leu Gln Glu
                275                 280                 285

Pro Ser Gln Pro Leu Asn Leu Thr Ala Lys Pro Lys Ala Pro Glu Leu
                290                 295                 300

Pro Asn Thr Ser Ser Ser Pro Ser Leu Lys Asn Ser Ser Cys Val Pro
305                 310                 315                 320

Arg Pro Pro Ser His Gly Gly Pro Thr Arg Asp Leu Gln Ser Ser Pro
                325                 330                 335

Pro Ser Leu Pro Leu Gly Phe Leu Gly Glu Gly Asp Ala Val Thr Lys
                340                 345                 350
```

```
Ala Ile Gln Asp Ala Arg Gln Leu Leu His Ser His Ser Gly Ala Leu
            355                 360                 365

Asp Gly Ser Pro Asn Thr Pro Phe Arg Lys Asp Leu Ile Ser Leu Asp
        370                 375                 380

Ser Ser Pro Ala Lys Glu Arg Leu Glu Asp Gly Cys Val His Pro Leu
385                 390                 395                 400

Glu Glu Ala Met Leu Ser Cys Asp Met Asp Gly Ser Arg His Phe Pro
                405                 410                 415

Glu Ser Arg Asn Ser Ser His Ile Lys Arg Pro Met Asn Ala Phe Met
            420                 425                 430

Val Trp Ala Lys Asp Glu Arg Arg Lys Ile Leu Gln Ala Phe Pro Asp
        435                 440                 445

Met His Asn Ser Ser Ile Ser Lys Ile Leu Gly Ser Arg Trp Lys Ser
    450                 455                 460

Met Thr Asn Gln Glu Lys Gln Pro Tyr Tyr Glu Glu Gln Ala Arg Leu
465                 470                 475                 480

Ser Arg Gln His Leu Glu Lys Tyr Pro Asp Tyr Lys Tyr Lys Pro Arg
                485                 490                 495

Pro Lys Arg Thr Cys Ile Val Glu Gly Lys Arg Leu Arg Val Gly Glu
            500                 505                 510

Tyr Lys Ala Leu Met Arg Thr Arg Arg Gln Asp Ala Arg Gln Ser Tyr
        515                 520                 525

Val Ile Pro Pro Gln Ala Gly Gln Val Gln Met Ser Ser Ser Asp Val
    530                 535                 540

Leu Tyr Pro Arg Ala Ala Gly Met Pro Leu Ala Gln Pro Leu Val Glu
545                 550                 555                 560

His Tyr Val Pro Arg Ser Leu Asp Pro Asn Met Pro Val Ile Val Asn
                565                 570                 575

Thr Cys Ser Leu Arg Glu Glu Gly Glu Gly Thr Asp Asp Arg His Ser
            580                 585                 590

Val Ala Asp Gly Glu Met Tyr Arg Tyr Ser Glu Asp Glu Asp Ser Glu
        595                 600                 605

Gly Glu Glu Lys Ser Asp Gly Glu Leu Val Val Leu Thr Asp
    610                 615                 620

<210> SEQ ID NO 5
<211> LENGTH: 483
<212> TYPE: PRT
<213> ORGANISM: Homo sapiens

<400> SEQUENCE: 5

Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Arg Tyr Trp Glu
            20                  25                  30

Thr Lys Gln Ala Phe Ile Lys Ala Thr Gly Lys Lys Glu Asp Glu His
        35                  40                  45

Val Val Ala Ser Asp Ala Asp Leu Asp Ala Lys Leu Glu Leu Phe His
    50                  55                  60

Ser Ile Gln Arg Thr Cys Leu Asp Leu Ser Lys Ala Ile Val Leu Tyr
65                  70                  75                  80

Gln Lys Arg Ile Cys Phe Leu Ser Gln Glu Glu Asn Glu Leu Gly Lys
                85                  90                  95
```

Phe Leu Arg Ser Gln Gly Phe Gln Asp Lys Thr Arg Ala Gly Lys Met
            100                 105                 110

Met Gln Ala Thr Gly Lys Ala Leu Cys Phe Ser Ser Gln Arg Leu
        115                 120                 125

Ala Leu Arg Asn Pro Leu Cys Arg Phe His Gln Glu Val Glu Thr Phe
    130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
            180                 185                 190

Lys Val Gln Thr Gln Val Arg Leu Ala Lys Lys Asn Phe Asp Lys Leu
        195                 200                 205

Lys Met Asp Val Cys Gln Lys Val Asp Leu Leu Gly Ala Ser Arg Cys
    210                 215                 220

Asn Leu Leu Ser His Met Leu Ala Thr Tyr Gln Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
            260                 265                 270

Pro Met Lys Lys Leu Val Glu Lys Glu Lys Lys Ile Asn Gln
        275                 280                 285

Gln Glu Ser Thr Asp Ala Ala Val Gln Glu Pro Ser Gln Leu Ile Ser
    290                 295                 300

Leu Glu Glu Glu Asn Gln Arg Lys Glu Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
        355                 360                 365

Asp Lys Asp Asp Leu Leu Leu Leu Ser Glu Ile Phe Asn Ala Ser Ser
    370                 375                 380

Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
            420                 425                 430

Gln Asn Met Lys Asp Leu Gln Ala Ser Leu Gln Glu Pro Ala Lys Ala
        435                 440                 445

Ala Ser Asp Leu Thr Ala Trp Phe Ser Leu Phe Ala Asp Leu Asp Pro
    450                 455                 460

Leu Ser Asn Pro Asp Ala Val Gly Lys Thr Asp Lys Glu His Glu Leu
465                 470                 475                 480

Leu Asn Ala

<210> SEQ ID NO 6
<211> LENGTH: 471
<212> TYPE: PRT
<213> ORGANISM: Homo sapiens -continued

<400> SEQUENCE: 6

```
Met Ser His His Pro Ser Gly Leu Arg Ala Gly Phe Ser Thr Ser
1               5                   10                  15

Tyr Arg Arg Thr Phe Gly Pro Pro Ser Leu Ser Pro Gly Ala Phe
            20                  25                  30

Ser Tyr Ser Ser Ser Arg Phe Ser Ser Arg Leu Leu Gly Ser
        35                  40                  45

Ala Ser Pro Ser Ser Val Arg Leu Gly Ser Phe Ser Pro Arg
50                  55                  60

Ala Gly Ala Gly Ala Leu Leu Arg Leu Pro Ser Glu Arg Leu Asp Phe
65                  70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
            100                 105                 110

Glu Lys Val Arg Phe Leu Glu Gln Gln Asn Ala Ala Leu Arg Gly Glu
        115                 120                 125

Leu Ser Gln Ala Arg Gly Gln Glu Pro Ala Arg Ala Asp Gln Leu Cys
130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
            180                 185                 190

Ala Glu His Asn Leu Val Leu Phe Arg Lys Asp Val Asp Asp Ala Thr
        195                 200                 205

Leu Ser Arg Leu Glu Leu Glu Arg Lys Ile Glu Ser Leu Met Asp Glu
210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
            260                 265                 270

Glu Ser Ile Ala Ala Lys Asn Leu Gln Glu Ala Glu Glu Trp Tyr Lys
        275                 280                 285

Ser Lys Tyr Ala Asp Leu Ser Asp Ala Ala Asn Arg Asn His Glu Ala
290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

Leu Arg Gln Leu Arg Glu Leu Glu Glu Gln Phe Ala Leu Glu Ala Gly
            340                 345                 350

Gly Tyr Gln Ala Gly Ala Ala Arg Leu Glu Glu Glu Leu Arg Gln Leu
        355                 360                 365

Lys Glu Glu Met Ala Arg His Leu Arg Glu Tyr Gln Glu Leu Leu Asn
370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415
```

```
-continued

Leu Asn Ile Lys Thr Thr Val Pro Glu Val Glu Pro Pro Gln Asp Ser
            420                 425             430

His Ser Arg Lys Thr Val Leu Ile Lys Thr Ile Glu Thr Arg Asn Gly
            435                 440             445

Glu Gln Val Val Thr Glu Ser Gln Lys Glu Gln Arg Ser Glu Leu Asp
    450                 455             460

Lys Ser Ser Ala His Ser Tyr
465             470
```